(12) United States Patent
Justis

(10) Patent No.: US 6,254,602 B1
(45) Date of Patent: Jul. 3, 2001

(54) ADVANCED COUPLING DEVICE USING SHAPE-MEMORY TECHNOLOGY

(75) Inventor: Jeff R. Justis, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/408,197

(22) Filed: Sep. 29, 1999

Related U.S. Application Data

(60) Provisional application No. 60/136,678, filed on May 28, 1999.

(51) Int. Cl.$^7$ .......................... A61B 17/56; A61B 17/68; A61B 17/70
(52) U.S. Cl. .................. 606/61; 606/53; 606/60
(58) Field of Search .................. 606/53, 60, 61, 606/72, 73

(56) References Cited

U.S. PATENT DOCUMENTS

| | | | |
|---|---|---|---|
| 4,379,575 | 4/1983 | Martin | 285/369 |
| 4,621,844 | 11/1986 | Kipp et al. | 285/381 |
| 5,176,680 | * 1/1993 | Vignaud et al. | 606/61 |
| 5,261,912 | * 11/1993 | Frigg | 606/61 |
| 5,474,555 | * 12/1995 | Puno et al. | 606/73 |
| 5,578,033 | * 11/1996 | Errico et al. | 606/61 |
| 5,584,834 | * 12/1996 | Errico et al. | 606/61 |
| 5,609,593 | * 3/1997 | Errico et al. | 606/61 |
| 5,672,176 | * 9/1997 | Biedermann et al. | 606/61 |
| 5,690,630 | * 11/1997 | Errico et al. | 606/61 |
| 5,733,285 | * 3/1998 | Errico et al. | 606/61 |
| 5,817,094 | * 10/1998 | Errico et al. | 606/61 |
| 5,882,350 | * 3/1999 | Ralph et al. | 606/61 |
| 5,964,760 | * 10/1999 | Richelsoph | 606/61 |
| 6,010,503 | * 1/2000 | Richelsoph et al. | 606/61 |
| 6,063,090 | * 10/2000 | Schlapfer | 606/61 |
| 6,077,262 | * 6/2000 | Schlapfer et al. | 606/61 |
| 6,132,432 | * 10/2000 | Richelsoph | 606/61 |
| 6,132,434 | * 10/2000 | Sherman et al. | 606/78 |

* cited by examiner

Primary Examiner—Gene Mancene
Assistant Examiner—Michael B. Priddy
(74) Attorney, Agent, or Firm—Woodard, Emhardt, Naughton, Moriarty & McNett

(57) ABSTRACT

An advanced coupling device using shape-memory technology. The coupling device includes a coupling element defining a longitudinal passage extending therethrough, the passage bounded by a side wall having a first end and an opposing second end, the side wall defining a first slot extending from the first end toward the second end, and a second slot extending from the second end toward the first end, and wherein a portion of the second slot is positioned proximately adjacent and longitudinally overlapping a portion of the first slot. The device further includes a compression element at least partially formed of a shape-memory material and being disposed about at least a portion of the coupling element. The compression element has a configuration which contracts about the coupling element and compresses the side wall against a member disposed within the passage to limit movement of the member relative to the coupling element.

57 Claims, 9 Drawing Sheets

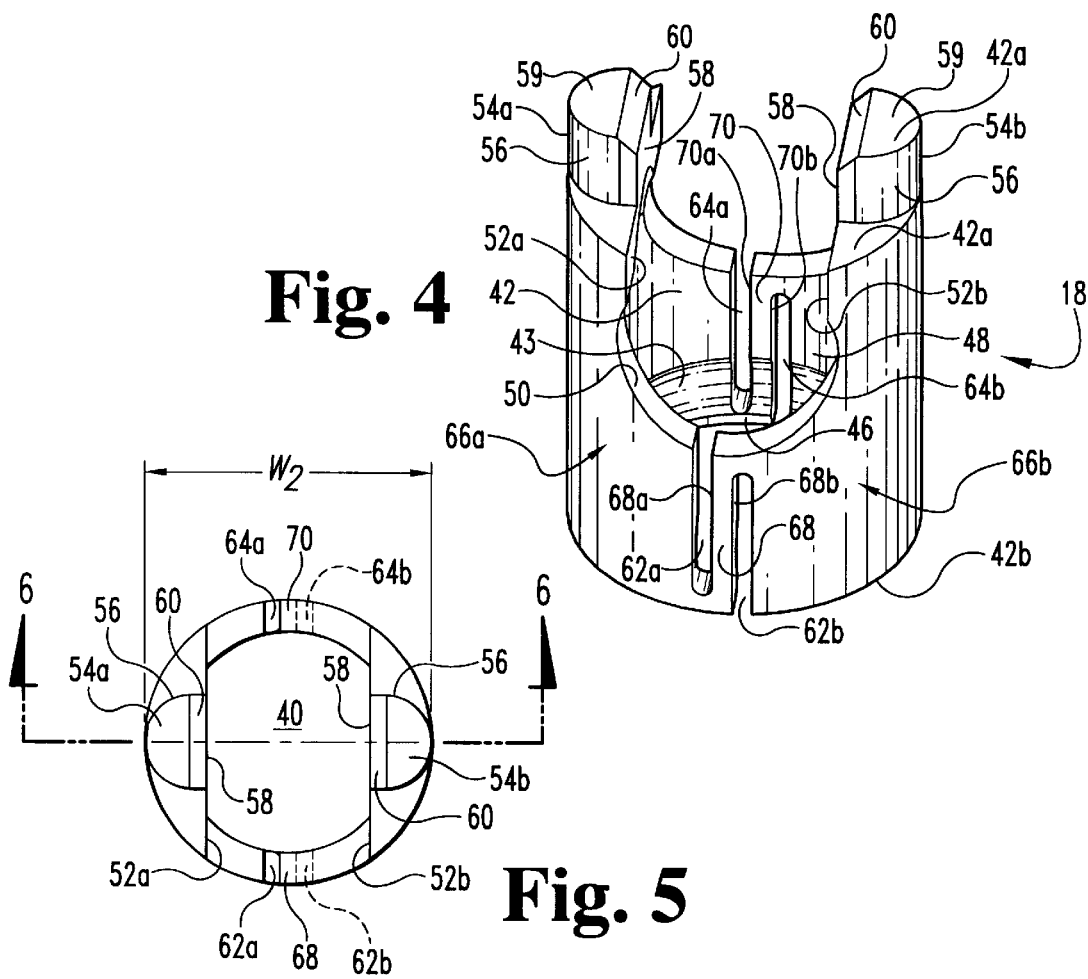
Fig. 4
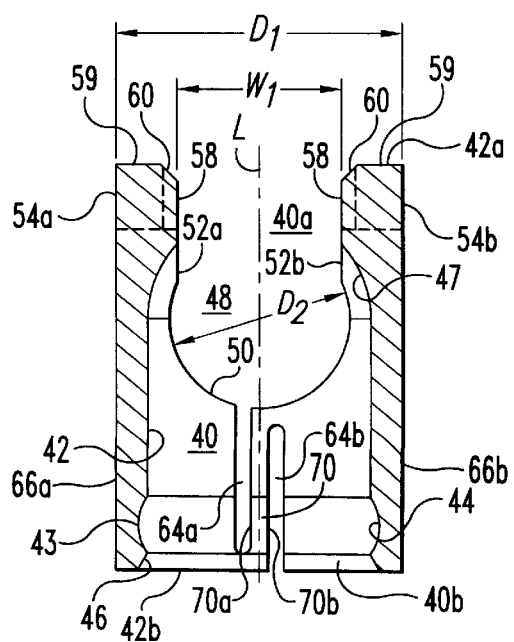
Fig. 5
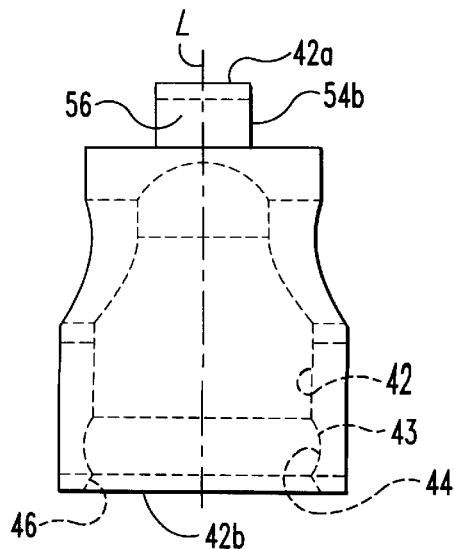
Fig. 6
Fig. 7

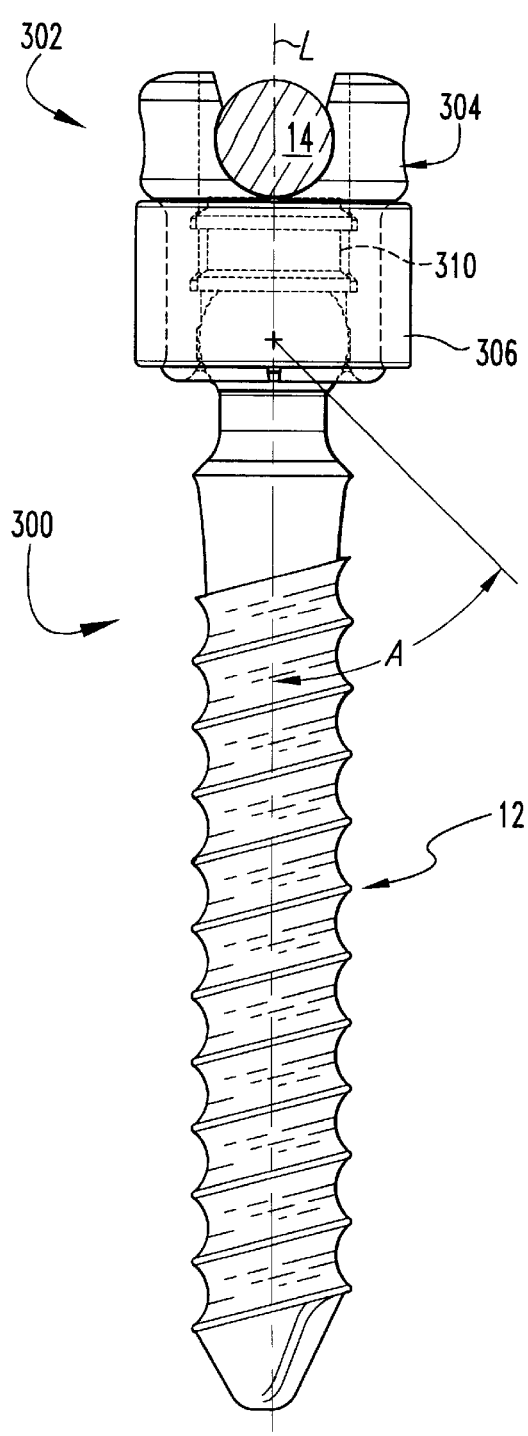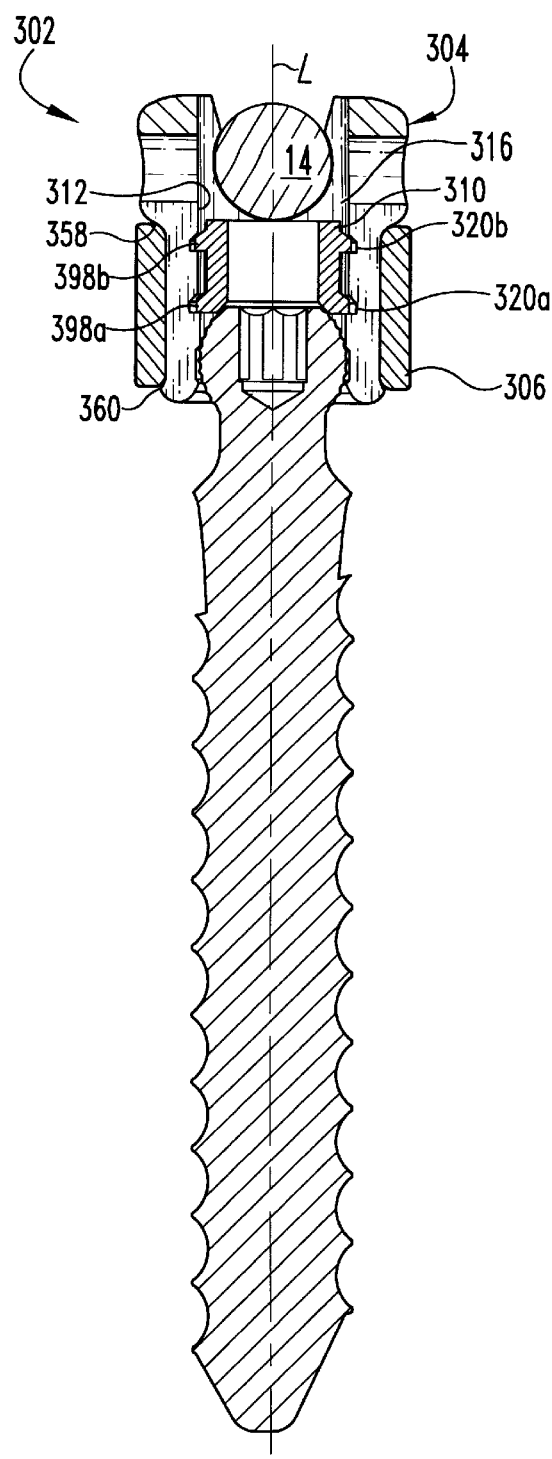
Fig. 19   Fig. 20

US 6,254,602 B1

ADVANCED COUPLING DEVICE USING SHAPE-MEMORY TECHNOLOGY

This application is based on provisional patent application Ser. No. 60/136,678, filed May 28, 1999, and priority is claimed in the present application to the extent the subject matter of this application is found in that provisional application. The content of that application is incorporated herein by reference.

FIELD OF THE INVENTION

The present invention broadly concerns an advanced coupling device using shape-memory technology. Specifically, but not exclusively, the invention concerns a spinal fixation system useful for engaging and connecting a plurality of vertebrae and capable of aligning a bone engaging fastener at multiple angular orientations with respect to an elongate member extending along a portion of the spine.

BACKGROUND OF THE INVENTION

Several techniques and systems have been developed for correcting and stabilizing the spine and for facilitating fusion at various levels of the spine. In one type of system, a bendable rod is disposed longitudinally along the length of the spine or vertebral column. The rod is preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of a vertebra. For instance, one such fixation element is a hook that is configured to engage the laminae of the vertebra. Other prevalent fixation elements include spinal screws or bolts that can be threaded into vertebral bone.

In one typical procedure utilizing a bendable spinal rod, the rod is situated on opposite sides of the spine or spinous processes. A plurality of fixation elements is attached to a portion of several vertebral bodies. The rods are then affixed to the plurality of fixation elements to thereby apply corrective and stabilizing forces to the spine.

One example of a rod-type spinal fixation system is the Cotrel-Dubosset/CD® Spinal System ("the CD® System") sold by Sofamor Danek Group, Inc. The CD® System provides a variety of fixation elements for engagement between an elongate rod and the spine. In one aspect of the CD® System, the fixation elements include a body that defines a slot within which the elongate rod is received. The slot includes a threaded bore into which a threaded plug is engaged in order to clamp the rod within the body of the fixation element. The CD® System includes hooks and bone screws with this "open-back" configuration. Details of this technology can be found in U.S. Pat. No. 5,005,562 to Dr. Cotrel. One benefit of this feature of the CD® System is that the fixation element is positioned directly beneath the elongate rod. This helps reduce the overall bulkiness of the implant construct and minimizes surgical trauma to surrounding tissue. However, the fixation elements of the CD® System are capable only of pivoting about the longitudinal axis of the elongate rod to achieve variable angular positions relative thereto. While this type of system is acceptable for many spinal pathologies, other cases require the fixation elements be angularly oriented in multiple planes relative to the axis of the rod. In other words, the fixation element must sometimes be allowed to pivot relative to the rod in a generally cone-shaped path. Screws of this type have been referred to as poly-axial or multi-axial bone screws.

Various poly-axial bone screw designs have been disclosed, generally including a receiver member configured to connect a bone screw having a curvate head to an elongate rod. The receiver member typically has a threaded portion adapted to threadedly engage a nut or set screw to thereby grip the head of the bone screw and connect the screw to the rod at a desired angular orientation. However, nuts and set screws have been known to have a tendency to back-out in in-vivo situations. This could likely cause the poly-axial bone screw assembly to loosen, thus requiring additional surgery. Moreover, the nuts and set screws may strip or gall, and their installation can be quite cumbersome due to the limited amount of space available to manipulate the tools necessary to drive the nuts and set screws into their engaged position. Furthermore, poly-axial bone screw designs of the past have typically required a multiplicity of parts that often make complete fixation of the bone screw a fairly complex process.

In recent years, a special material known as "shape-memory alloy" has been used in the construction of various mechanical devices. This type of material is an alloy of known metals, such as copper and zinc, nickel and titanium, silver and cadmium, and others, that are known to exhibit a "shape-memory" characteristic in which a particular component formed of a shape-memory alloy ("SMA") is capable of reforming to a "memorized" shape at certain temperatures. This phenomena occurs when the SMA alloy changes from a martensitic crystal phase to an austenitic crystal phase. In the martensite stage, the SMA is relatively weak and pliable. As the temperature of the SMA component is increased above its transformation temperature range, the SMA transforms to an austenitic stage and the material becomes relatively strong with super-elastic properties. Generally, the strength and super-elastic characteristics of a shape-memory material tend to increase toward the high temperature end of the transformation temperature range, and decrease toward the low temperature end. While there are many alloys that exhibit shape-memory characteristics, one of the more common SMAs is an alloy of nickel and titanium. One such well known alloy is Nitinol®, which has proven to be highly effective for devices to be placed within the human body because its transformation temperature range falls between room temperature and normal human body temperature.

There is a general need in the industry to provide an advanced coupling device which uses shape-memory technology to connect two or more members. There is also a more specific need to provide an improved multi-axial bone engaging fastener using shape-memory technology. This need also encompasses a goal of minimizing the profile and bulk of the components used to attach the bone engaging fastener to a vertebra and to further connect the bone engaging fastener to an elongate member. Furthermore, it is desirable to reduce the number of components that must be manipulated by the surgeon during a surgical procedure. The present invention meets these general and specific needs and provides other benefits and advantages in a novel and unobvious manner.

SUMMARY OF THE INVENTION

The present invention relates generally to an advanced coupling device for connecting two or more members using shape-memory technology. While the actual nature of the invention covered herein can only be determined with reference to the claims appended hereto, certain forms of the invention that are characteristic of the preferred embodiments disclosed herein are described briefly as follows.

In one form of the present invention, a coupling device is provided for connection to a member, including a coupling element and a compression element. The coupling element defines a longitudinal passage extending therethrough, the passage bounded by a side wall having a first end and a second end. The side wall defines a first slot extending from the first end toward the second end, and a second slot extending from the second end toward the first end. A portion of the second slot is positioned proximately adjacent and longitudinally overlapping a portion of the first slot. The compression element is at least partially formed of a shape-memory material and is disposed about a portion of the coupling element. The compression element has a first configuration at one temperature and a second configuration at a different temperature. The second configuration contracts about the coupling element and compresses the side wall against the member, thus limiting movement of the member relative to the coupling element. In a further aspect of the invention, the coupling element is adapted for connection to a second member.

In another form of the present invention, a fixation system is provided which includes an elongate member, a bone engaging member having an at least partially spherical-shaped head and a portion configured to engage bone, and a coupling element and compression element adapted to connect the bone engaging member to the elongate member. The coupling element defines a longitudinal passage extending therethrough, the passage being bounded by a side wall having a first end and an opposing second end. The coupling element also defines a channel extending laterally therethrough and sized to receive the elongate member therein. The channel intersects the passage and has an opening at the second end for receiving the elongate member. The side wall defines a first slot extending from the first end toward the second end, and a second slot extending from the second end toward the first end. A portion of the second slot is positioned proximately adjacent and longitudinally overlapping a portion of the first slot. The compression element is at least partially formed of a shape-memory material and is disposed about a portion of the coupling element. The compression element has a first configuration at one temperature and a second configuration at a different temperature. The second configuration contracts about the coupling element and compresses the side wall against the head of the bone engaging member to limit movement of the bone engaging member relative to the coupling element. In one aspect of the invention, the side wall defines an inner recess for receiving the head of the bone engaging member therein so that the angular alignment of the bone engaging member may be variably adjusted relative to the coupling element when a compression element is in its first configuration. In a further aspect of the invention, the fixation system further includes a locking element at least partially formed of a shape-memory material and disposed about another portion of the coupling element adjacent the channel. The locking element has a first configuration at one temperature and a second configuration at a different temperature. The second configuration contracts about the coupling element and compresses the side wall against the elongate member to thereby limit movement of the elongate member relative to the coupling element.

In a further form of the present invention, a coupling device is provided for connection to a member, including a coupling element defining a longitudinal passage extending therethrough and including slot means for rendering the passage collapsible. A shape-memory means cooperates with the coupling element to allow movement of the member relative to the coupling element when at one temperature, and limiting movement of the member relative to the coupling element when at a second temperature. In a further aspect of the invention, the coupling device includes means for connecting the coupling element to a second member.

In an additional form of the present invention, a coupling device is provided for connection to a member, including a coupling element having two integrally formed longitudinal segments. The segments define a longitudinal passage extending through the coupling element. The segments are connected by a narrow beam of material having first and second edges extending generally in a longitudinal direction. The coupling device further includes a compression element at least partially formed of a shape-memory material and disposed about at least a portion of the two longitudinal segments. The compression element has a first configuration at one temperature and a second configuration at a different temperature. The second configuration contracts about the longitudinal segments and compresses the segments against the member disposed within the passage to limit movement of the member relative to the coupling element. In a further aspect of the invention, the coupling element is adapted for connection to a second member.

In yet another form of the present invention, a coupling device is provided for connection to a member, including a coupling element and a compression element. The coupling element defines a longitudinal passage extending therethrough, the passage bounded by a side wall having a first end and a second end. The side wall defines a first slot extending from the first end toward the second end and including first and second segments, and a second slot extending from the second end toward the first end and having a portion positioned intermediate the first and second segments of the first slot. The compression element is at least partially formed of a shape-memory material and is disposed about a portion of the coupling element. The compression element has a first configuration at one temperature and a second configuration at a different temperature. The second configuration contracts about the coupling element and compresses the side wall against the member, thus limiting movement of the member relative to the coupling element.

It is one object of the present invention to provide an advanced coupling device using shape-memory technology.

Another object of the present invention is to provide an advanced coupling device for use in a spinal fixation system for connecting a bone engaging member to an elongate member.

Further objects, features, advantages, benefits, and aspects of the present invention will become apparent from the drawings and description contained herein.

BRIEF DESCRIPTION OF THE DRAWINGS

FIG. 4 is a top perspective view of one embodiment of a coupling element used with the system depicted in FIG. 1.

FIG. 5 is a top view of the coupling element shown in FIG. 4.

FIG. 6 is a side cross-sectional view of the coupling element shown in FIG. 4 taken along line 6—6 of FIG. 5.

FIG. 7 is an end elevational view of the coupling element shown in FIG. 4.

FIG. 19 is an elevation view of a spinal fixation system according to yet another embodiment of the present invention.

FIG. 20 is a cross-sectional view of the system depicted in FIG. 19.

DESCRIPTION OF THE PREFERRED EMBODIMENTS

Figure 1:
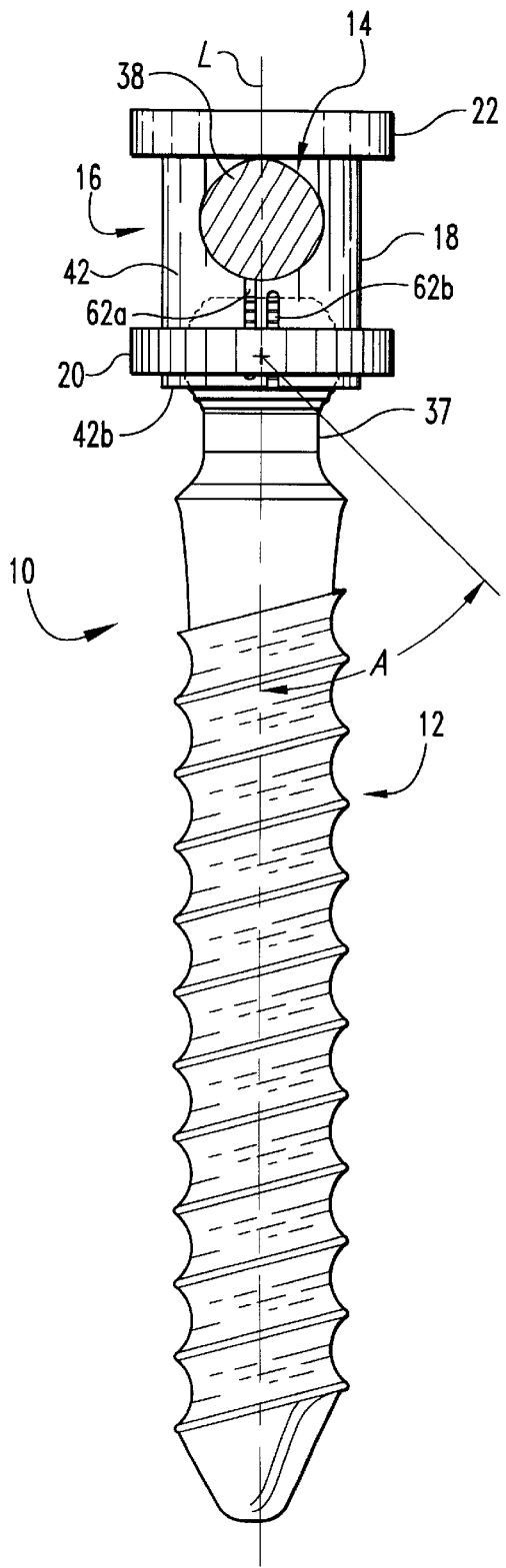
FIG. 1 is an elevational view of a spinal fixation system according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated device, and any further applications of the principles of the invention as illustrated therein being contemplated as would normally occur to one skilled in the art to which the invention relates.

FIG. 1 depicts a spinal fixation system 10 according to a preferred embodiment of the present invention. System 10 includes a bone engaging member 12, an elongate member 14 and a coupling device 16 for connecting bone engaging member 12 to elongate member 14. In a typical application, a pair of elongate members 14 are situated on opposite sides of the spinal column and a plurality of bone engaging members 12 are attached to two or more vertebral bodies and affixed along the length of elongate members 14. It should be understood that, although it is preferable to attach an elongate member 14 to each side of the spinal column, a single elongate member 14 can be attached to one side of the spinal column. System 10 can be used in a variety of applications associated with the spine to address a wide range of spinal pathologies. For example, application of system 10 may be limited to the lumbar region of the spine for fixation following a diskectomy. Alternatively, system 10 can extend substantially along the entire length of the thoracic and lumbar regions of the spine to correct various deformities, such as scoliosis. In other applications, system 10 may provide fixation and stabilization of the cervical spine, such as might occur following a fracture or dislocation. It is of course understood by a person of ordinary skill in the art that the configuration of the components of system 10 will vary depending upon the region of the spine to be treated and the type of treatment to be administered.

In accordance with the present invention, engagement between elongate member 14 and one or more vertebrae may require orientation of bone engaging member 12 at a wide range of three-dimensional angles relative to elongate member 14. In some circumstances, it may be difficult to situate elongate member 14 in an optimum spatial relationship relative to the vertebrae. In this instance, engagement of bone engaging member 12 to the spinal column may require bone engaging member 12 to assume various angular orientations relative to elongate member 14, including orientations not possible through the use of prior devices and systems.

Figure 2:
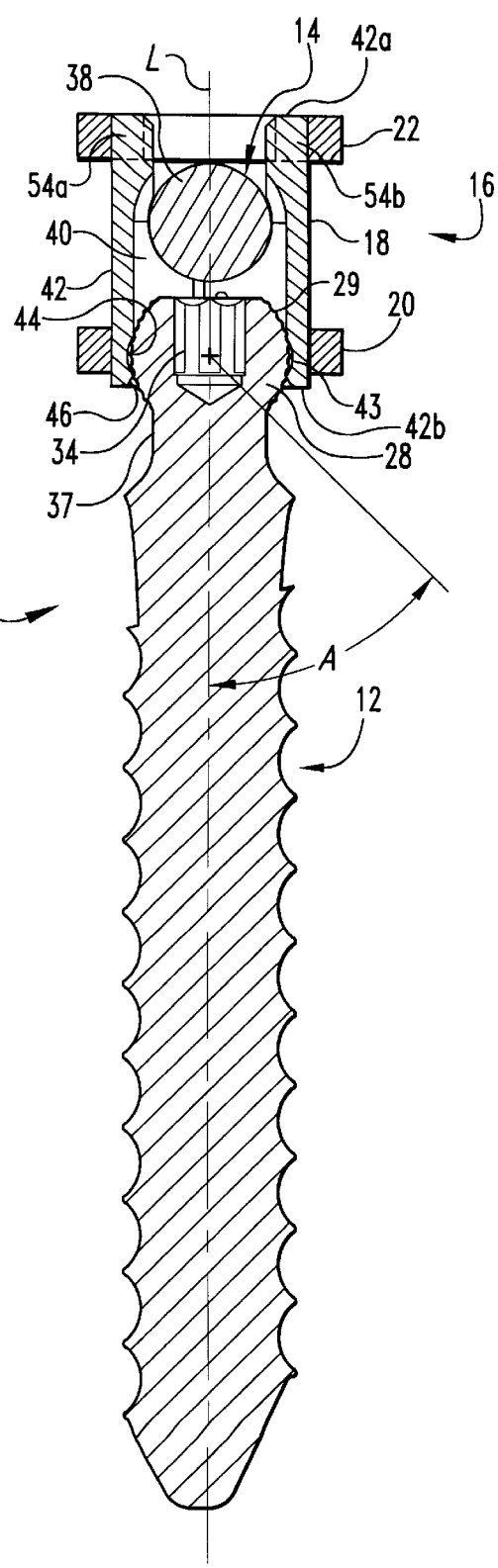
FIG. 2 is a cross-sectional view of the system depicted in FIG. 1.

Referring now to FIGS. 1 and 2, bone engaging member 12 is shown connected to elongate member 14 by way of coupling device 16. In a preferred embodiment, coupling device 16 includes a coupling element 18 defining a longitudinal axis L, a compression element 20, and a locking element 22. Coupling element 18 is configured to receive a portion of bone engaging member 12 and elongate member 14 therein. Compression element 20 and locking element 22 are disposed about a portion of coupling element 18 and aligned generally along longitudinal axis L. In one embodiment of coupling device 16, bone engaging member 12 is capable of assuming a wide range of angles, up to angle A, relative to longitudinal axis L. Although angle A is illustrated in FIGS. 1 and 2 as lying in a single plane (i.e., in the plane of the paper face), it should be understood that bone engaging member 12 is capable of pivoting through a generally cone-shaped path relative to longitudinal axis L. In one working configuration of coupling device 16, bone engaging member 12 is allowed to freely rotate and pivot relative to coupling element 18, and in another working configuration, coupling element 18 is compressed against a portion of bone engaging member 12, thereby limiting movement of bone engaging member 12 relative to coupling element 18. Similarly, in one working configuration of coupling device 16, elongate member 14 is allowed to rotate and translate relative to coupling element 18, and in another working configuration, coupling element 18 is compressed against a portion of elongate member 14, thereby limiting movement of elongate member 14 relative to coupling element 18.

Figure 3:
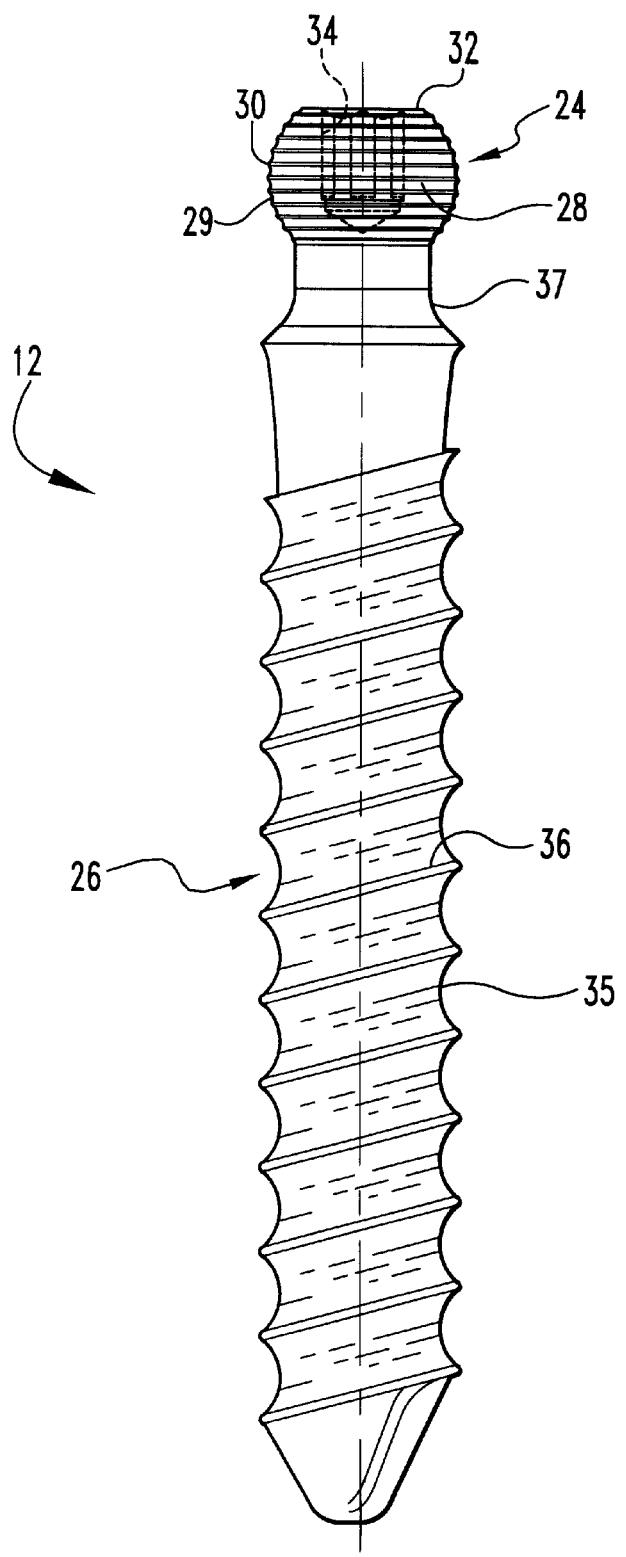
FIG. 3 is an elevational view of a bone screw adapted for use with the system depicted in FIG. 1.

Referring now to FIG. 3, shown therein are various structural details of bone engaging member 12. Bone engaging member 12 includes a connecting portion 24 and an engaging portion 26 extending therefrom. Preferably, connecting portion 24 includes an at least partially spherical-shaped head 28. Head 28 defines a substantially spherical surface 29 which provides for bearing contact with coupling element 18 so that bone engaging member 12 can be aligned at a variety of angular orientations relative to longitudinal axis L. Although head 28 is shown to be substantially spherical-shaped, it should be understood that spherical surface 29 can take on a variety of shapes and configurations, such as an elliptical shape or a number of other arcuate configurations.

In one specific embodiment of bone engaging member 12, head 28 defines a plurality of tool marks 30 disposed about the periphery of head 28. Head 28 includes a truncated, flat upper surface 32 through which is defined a tool receiving recess 34, and which may be configured to accept any type of known driving tool. Preferably, but not necessarily, tool receiving recess 34 is a hex recess sized to receive the hex end of a driving tool so that bone engaging member 12 may be driven into a vertebral body. Engaging portion 26 includes a threaded shank 35 that carries threads 36. Preferably, threads 36 are cancellous threads configured to engage a vertebral body. Although engaging portion 26 is illustrated as being a threaded shank, it should be understood that engaging portion 26 can take on other configurations, such as, for example, a hook capable of engaging various aspects of a vertebral body. In a further aspect of bone engaging member 12, an annular relief 37 is provided between head 28 and threaded shank 35. Referring back to FIGS. 1 and 2, it can be seen that annular relief 37 is configured to allow bone engaging member 12 to have a wider range of angular movement relative to longitudinal axis L by avoiding contact between threaded shank 35 and the bottom end of coupling element 18.

As depicted in FIGS. 1 and 2, elongate member 14 includes a connecting portion 38 sized to be received within a portion of coupling element 18. In a preferred embodiment, elongate member 14 is a spinal rod configured to extend along a portion of the spinal column. Although connecting portion 38 is shown as having a generally circular outer cross section, it should be understood that connecting portion 38 can take on a variety of alternative shapes, such as, for example, a square, an ellipse, or a number of other polygonal configurations.

Referring now to FIGS. 4–7, shown therein are various structural details of coupling element 18. Coupling element 18 includes a passage 40 extending therethrough generally along longitudinal axis L, thus defining an upper opening 40a and a lower opening 40b (FIG. 6). Preferably, but not necessarily, coupling element 18 is substantially cylindrical-shaped and defines an outer diameter $D_1$. Passage 40 is bounded by a side wall 42 having a first end 42a and an opposing second end 42b. Side wall 42 defines an inner annular recess 43 adapted to receive head 28 therein so that the angular alignment of bone engaging member 12 may be variably adjusted relative to longitudinal axis L of coupling element 18. Inner recess 43 includes a peripheral, partially spherical surface 44, generally corresponding to spherical surface 29 of head 28. Partially spherical surface 44 contacts only a portion of spherical surface 29 when head 28 is disposed within inner recess 43. In other words, the radius of spherical surface 44 is smaller than the radius of spherical surface 29. In this embodiment, only the outer edges of inner recess 43 contact spherical surface 29. Preferably, but not necessarily, inner recess 43 is positioned along passage 40 adjacent second end 42b, and side wall 42 further defines an inner tapered surface 46 extending outwardly from inner recess 43 to second end 42b. Passage 40 preferably, but not necessarily, includes an upper peripheral, partially spherical surface 47 disposed between inner recess 43 and first end 42a.

Referring back to FIG. 2, it can be seen that tapered surface 46 provides an enhanced range of movement of bone engaging member 12 relative to coupling element 18 as spherical head 28 is pivotally rotated within inner recess 43. Tapered surface 46 thus permits bone engaging member 12 to be rotated up to angle A relative to longitudinal axis L. In accordance with a preferred embodiment, tapered surface 46 communicates with inner recess 43 at an inner diameter that is slightly less than the outer diameter of head 28. In this manner, in order for head 28 to be received within inner recess 43, side wall 42 must be slightly outwardly deformed to expand passage 40 to a size sufficient to accept head 28 within inner recess 43. Once head 28 is positioned within inner recess 43, side wall 42 is allowed to snap back into its original, undeformed state. The elastic characteristics of coupling element 18 thus provisionally maintain head 28 within inner recess 43.

Referring again to FIGS. 4–7, it can be seen that coupling element 18 defines a channel 48 extending laterally therethrough. Channel 48 intersects passage 40 and is preferably aligned generally perpendicular to longitudinal axis L. Channel 48 is bounded by a concave bottom surface 50 and opposing flat surfaces 52a, 52b. Flat surfaces 52a, 52b communicate between concave bottom surface 50 and upper opening 40a of passage 40, thus defining a substantially U-shaped channel. Concave bottom surface 50 has a channel diameter $D_2$ that is preferably substantially equal to the outer diameter of connecting portion 38 of elongate member 14.

Opposing flat surfaces 52a, 52b define a channel width $W_1$ that is preferably slightly smaller than the outer diameter of connecting portion 38.

Elongate member 14 may be received within channel 48 by either sliding elongate member 14 through channel 48 along concave bottom surface 50 transverse to longitudinal axis L or, alternatively, by sliding elongate member 14 between opposing flat surfaces 52a, 52b and slightly deforming side wall 42 so that surfaces 52a, 52b are splayed apart far enough to accept elongate member 14 therebetween. Elongate member 14 can then be slid along longitudinal axis L toward concave bottom surface 50. Once elongate member 14 is positioned adjacent concave bottom surface 50, side wall 42 is allowed to snap back into its original, undeformed state. In this manner, elongate member 14 can be provisionally maintained within channel 48. However, it should be understood that channel diameter $D_2$ and channel width $W_1$ can alternatively be substantially equal. It should also be understood that, while channel diameter $D_2$ and channel width $W_1$ are shown to be smaller than the maximum diameter of passage 40, either or both can be sized slightly larger than the maximum diameter of passage 40. Additionally, channel 48 is positioned sufficiently apart from inner recess 43 so that when head 28 of bone engaging member 12 is received within inner recess 43, head 28 will not intersect channel 48 and contact elongate member 14.

Coupling element 18 includes a pair of opposing fingers 54a, 54b extending from side wall 42. Each of fingers 54a, 54b includes a rounded portion 56 facing outwardly from channel 48, and a flat portion 58 aligned generally flush with a corresponding one of opposing flat surfaces 52a, 52b. Opposing fingers 54a, 54b define a maximum outer width $W_2$, as measured between rounded portions 56, that is preferably substantially equal to outer diameter $D_1$ of coupling element 18. Each of opposing fingers 54a, 54b also defines a top surface 59 and an angled surface 60 extending between top surface 59 and flat portion 58. Angled surfaces 60 serve to aid in guiding elongate member 14 between flat portions 58 and into channel 48.

Side wall 42 of coupling element 18 defines a first slot 62a extending from first end 42a toward second end 42b. Side wall 42 also defines a second slot 62b extending from second end 42b toward first end 42a. A portion of second slot 62b is positioned proximately adjacent and longitudinally overlapping a portion of first slot 62a. In other words, a plane aligned perpendicular to longitudinal axis L and positioned at a select location along longitudinal axis L would intersect both first slot 62a and second slot 62b. Preferably, but not necessarily, first slot 62a terminates at a location proximately adjacent second end 42b. Similarly, second slot 62b preferably terminates at a location proximately adjacent concave bottom surface 50 of channel 48. However, it should be understood that only a relatively small portion of first slot 62a need be positioned proximately adjacent and longitudinally overlapping second slot 62b.

First slot 62a and second slot 62b are preferably aligned substantially parallel to one another. However, it should be understood that first and second slots 62a, 62b may alternatively be aligned in a non-parallel configuration. It should also be understood that slots 62a, 62b need not necessarily be straight, but can take on angled or curved configurations as well. In a preferred embodiment, first and second slots 62a, 62b are aligned substantially parallel to one another and aligned generally along longitudinal axis L. Preferably, but not necessarily, side wall 42 defines a second pair of slots 64a, 64b configured substantially similar to first and second slots 62a, 62b. Second pair of slots 64a, 64b are preferably positioned generally opposite first and second slots 62a, 62b. In other words, slots 64a, 64b are positioned in diametric opposition relative to first and second slots 62a, 62b. In the embodiment shown, first slot 62a defines channel 48. In other words, channel 48 is considered to be part of first slot 62a. However, it should be understood that first slot 62a may alternatively be positioned along side wall 42 without intersecting channel 48.

Coupling element 18 is thus comprised of two integrally formed longitudinal segments 66a, 66b. Segments 66a, 66b define passage 40 and are connected by generally opposing narrow sections of material 68, 70. Section 68 has first and second edges 68a, 68b which preferably extend generally along longitudinal axis L. Section 70 has first and second edges 70a, 70b which also preferably extend generally along longitudinal axis L. Although first and second edges 68a, 68b are shown to be aligned substantially parallel, it should be understood that they may alternatively be aligned in a non-parallel configuration. Additionally, although first and second edges 68a, 68b are shown aligned generally along longitudinal axis L, it should be understood that either one or both of edges 68a, 68b may be aligned transverse to longitudinal axis L (i.e., crossing longitudinal axis L). It should also be understood that although edges 68a, 68b are illustrated as being generally straight, they may alternatively take on other configurations, such as angled or curved. Similarly, first and second edges 70a, 70b of section 70 can take on any of the configurations described immediately above regarding edges 68a, 68b. Moreover, although a preferred embodiment contemplates segments 68, 70 as being generally symmetrical (i.e., configured as longitudinal halves), it should be understood that segments 68, 70 can alternatively take on non-symmetrical configurations as well. In other words, narrow section of material 68 does not necessarily have to be positioned in diametric opposition to narrow section of material 70.

Referring back to FIGS. 1 and 2, it can be seen that compression element 20 and locking element 22 are disposed about a portion of coupling element 18 and are generally aligned along longitudinal axis L. Compression element 20 is preferably positioned adjacent second end 42b of side wall 42 within the same transverse plane as inner recess 43. Additionally, compression element 20 is preferably disposed about at least a portion of the longitudinally overlapping portions of slots 62a, 62b and slots 64a, 64b. Locking element 22 is preferably positioned adjacent first end 42a of side wall 42 and disposed about rounded portions 56 of opposing fingers 54a, 54b.

Compression element 20 and locking element 22 are at least partially formed of a shape-memory material such as, for example, Nitinol®, a bio-compatible shape-memory metal alloy of nickel and titanium. It is well known in the art that articles made of such shape-memory materials are pliable and can typically be readily reshaped at temperatures below their transformation temperature range. Such articles can be trained to have a pre-programmed shape (commonly referred to as a "memorized shape") which the article will change into when the shape-memory material reaches a temperature above its transformation temperature range. After reaching such a temperature, the article will attempt to return to its pre-programmed, memorized shape. In so doing, the article converts heat energy into mechanical work. There is a wide variety of shape-memory materials, including shape-memory metal alloys (e.g., titanium based alloys and iron based alloys) and shape-memory polymers, which have a wide range of possible transformation temperature ranges. Selection of an appropriate shape-memory material will depend, in large part, on the required material properties for the particular application as well as the working environment of the device. Nitinol® is well suited for the particular application of the present invention because it provides a transformation temperature range between room temperature and normal body temperature. Moreover, Nitinol® has a very low corrosion rate, which provides an advantage when used within the human body. Additionally, implant studies in animals have shown minimal elevations of nickel in the tissues in direct contact with the Nitinol® material. However, it should be understood that other medical grade shape-memory materials could alternatively be used in place of Nitinol®.

Figure 8:
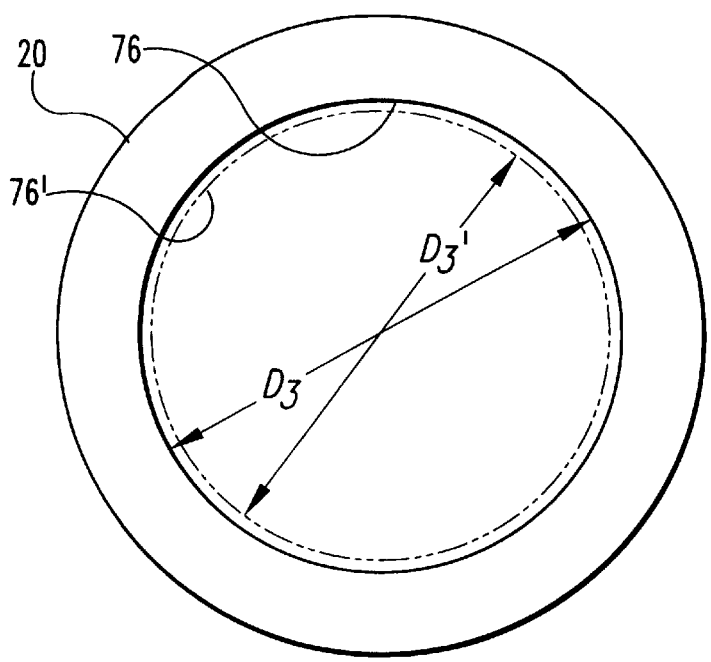
FIG. 8 is a top view of one embodiment of a shape-memory ring used with the system depicted in FIG. 1.

Referring now to FIG. 8, shown therein are various structural details of compression element 20. Compression element 20 is generally ring-shaped and defines an inner diameter $D_3$. It should be understood that while compression element 20 is depicted as a circular ring, other shapes and configurations are also contemplated as would occur to one of ordinary skill in the art. When the shape-memory material within compression element 20 is in its martensitic or room temperature state, inner diameter $D_3$ is slightly larger than outer diameter $D_1$ of coupling element 18. In other words, compression element 20 includes an inner annular surface 76 that preferably corresponds to the outer surface of side wall 42, such that compression element 20 can be easily slid over side wall 42 when the shape-memory material is at a temperature below its transformation temperature range (i.e., when the shape-memory material is in its martensitic or room temperature state).

Figure 9:
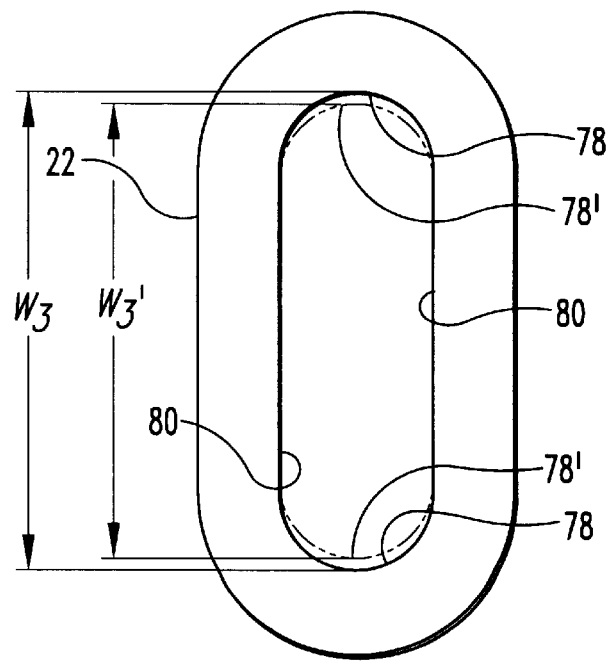
FIG. 9 is a top view of another embodiment of a shape-memory ring used with the system depicted in FIG. 1.

Referring to FIG. 9, shown therein are various structural details of locking element 22. Locking element 22 is at least partially formed of a shape-memory material such as, for example, Nitinol®. Preferably, but not necessarily, the shape-memory material of compression element 20 and the shape-memory material of locking element 22 have the same composition. Locking element 22 is an oblong ring having opposing curved inner surfaces 78 and opposing, generally flat inner surfaces 80 positioned intermediate curved inner surfaces 78. Curved inner surfaces 78 generally correspond to rounded portions 56 of opposing fingers 54a, 54b and define a maximum width $W_3$ therebetween. It should be understood that while locking element 22 is depicted as an oblong ring, other shapes and configurations are also contemplated as would occur to one of ordinary skill in the art. For instance, locking element 22 may take on a circular configuration similar to compression element 20. When the shape-memory material within locking element 22 is in its martensitic or room temperature state, inner width $W_3$ is slightly greater than outer width $W_2$ of opposing fingers 54a, 54b. In other words, curved inner surfaces 78 are separated by a sufficient distance such that locking element 22 can be easily slid over opposing fingers 54a, 54b when the shape-memory material is at a temperature below its transformation temperature range.

Referring back to FIGS. 1–2, in one specific embodiment, spinal fixation system 10 is assembled by positioning head 28 of bone engaging member 12 within inner recess 43 of coupling element 18, such that spherical surface 29 is positioned adjacent spherical surface 44. Compression element 20 is positioned about coupling element 18 and, as described above, is preferably positioned in the same plane as inner recess 43 and disposed about at least a portion of the longitudinally overlapping portions of slots 62a, 62b and slots 64a, 64b. This initial assembly may then be introduced into the surgical site and threaded shank 35 of bone engaging member 12 may be threadedly driven into a portion of a vertebral body according to the protocol for the particular spinal procedure. Specifically, a driving tool (not shown) may be received through passage 40 and aligned with tool receiving recess 34 of head 28. Bone engaging member 12 may then be driven into a vertebral body to a recommended depth for adequate fixation, but preferably not so deep that second end 42b of side wall 42 contacts or presses against the vertebral body. In order for the multi-axial capability of system 10 to be realized, bone engaging member 12 must be free to pivot in three dimensions relative to longitudinal axis L. As discussed above, in accordance with a preferred embodiment, tapered surface 46 communicates with inner recess 43 at an inner diameter that is slightly less than the outer diameter of spherical head 28, and thus side wall 42 must be slightly splayed apart in order for head 28 to be received within inner recess 43. When head 28 is received within inner recess 43, bone engaging member 12 is provisionally connected to coupling element 18.

With bone engaging member 12 provisionally connected to coupling element 18 and adequately affixed to a vertebral body, connecting portion 38 of elongate member 14 may be introduced into channel 48 and positioned adjacent concave bottom surface 50. As discussed above, coupling element 18 is preferably configured so that connecting portion 38 does not contact any portion of head 28 of bone engaging member 12, regardless of the relative angle A between longitudinal axis L and bone engaging member 12. Once connecting portion 38 is properly positioned within channel 48, locking element 22 may then be positioned about opposing fingers 54a, 54b. As discussed above, in accordance with a preferred embodiment, opposing flat surfaces 52a, 52b define a channel width $W_1$ that is slightly smaller than the outer diameter of connecting portion 38, and thus side wall 42 must be slightly splayed apart in order for elongate member 14 to be received within channel 48. When connecting portion 38 is received within channel 48, elongate member 14 is provisionally connected to coupling element 18.

Although the preceding paragraphs set forth a description of a specific procedure for assembling system 10, it should be understood that other procedures are also contemplated as would occur to one of ordinary skill in the art, and that the above discussion in no way limits the scope of protection sought.

While the shape-memory material within each of compression element 20 and locking element 22 is at or below its transformation temperature range, bone engaging member 12 will be allowed to freely rotate and pivot in any direction relative to longitudinal axis L. Similarly, elongate member 14 will be allowed to freely rotate and translate within channel 48. It should be understood that, prior to insertion of compression element 20 and locking element 22 within the patient, the respective temperatures of compression element 20 and locking element 22 are below the transformation temperature range and the shape-memory material is in its martensitic state. At this stage, compression element 20 has a first configuration, as depicted in FIG. 8, wherein inner annular surface 76 defines inner diameter $D_3$ and locking element 22 has a first configuration, as depicted in FIG. 9, wherein curved inner surfaces 78 define a maximum inner width $W_3$.

Once bone engaging member 12 and elongate member 14 are positioned at a desired position and orientation relative to coupling element 18, compression element 20 and locking element 22 are heated up in a manner to be described below. As the temperature of the shape-memory material is increased beyond the transformation temperature range, the shape-memory material shifts from its martensitic state to its austenitic state. In the austenitic state, compression element 20 and locking element 22 are each reformed into a second configuration. Referring to FIG. 8, in the austenitic state, compression element 20 is reformed into a second configuration in which its inner diameter is reduced to $D_3'$, as defined by inner annular surface 76' (shown in phantom). Referring to FIG. 9, in the austenitic state, locking element 22 is reformed into a second configuration in which its maximum inner width is reduced to $W_3'$, as reflected by curved inner surfaces 78' (shown in phantom). Although FIG. 9 illustrates the reformation of locking element 22 as including only the shortening of flat inner surfaces 80, it should be understood that, in an alternative embodiment, the distance separating flat inner surfaces 80 can also be reduced as locking element 22 is reformed from its first configuration into its second configuration (i.e., the size and configuration of curved inner surfaces 78 may be reformed concurrently with flat inner surfaces 80).

Once bone engaging member 12 is positioned at a desired angular orientation relative to longitudinal axis L, compression element 20 is heated up. As compression element 20 is reformed into its second configuration at a temperature above the transformation temperature range of the shape-memory material, compression element 20 will contract about coupling element 18. As compression element 20 engages and tightens about coupling element 18, side wall 42 will correspondingly compress tightly against bone engaging member 12, and more specifically head 28. The super-elastic properties of the shape-memory material enable significant recoverable strains, and therefore compression forces, to be developed by compression element 20. These forces are transmitted to side wall 42, which in turn tightly engages head 28, thereby limiting movement of bone engaging member 12 relative to coupling element 18. Thus, after compression element 20 is reformed into its second configuration, head 28 will no longer be allowed to freely rotate within inner recess 43 and will no longer be allowed to freely pivot relative to longitudinal axis L. Hence, one function of slots 62a, 62b and slots 64a, 64b is to render passage 40 readily collapsible. Thus, as compression element 20 contracts about coupling element 18, the maximum compression force generated by compression element 20 will be applied to the interface between head 28 of bone engaging member 12 and inner recess 43 of side wall 42. Slots 62a, 62b and slots 64a, 64b ensure that the recovered stress in compression element 20 will generate the maximum contact pressure between head 28 and inner recess 43. As discussed above, compression element 20 is preferably positioned in the same transverse plane as inner recess 43, and placed adjacent at least a portion of the longitudinally overlapping portions of slots 62a, 62b and 64a, 64b. This desired positioning also aids in securely clamping head 28 within inner recess 43.

Although there are various ways in which to increase the temperature of the shape-memory material above its transformation temperature range, in one specific embodiment of the present invention, when compression element 20 is placed within a patient, the body temperature of the patient will increase the temperature of the shape-memory material and cause it to shift from its martensitic state to its austenitic state. However, it should be understood that the temperature of the shape-memory material may be increased above its transformation temperature range by running electrical current through compression element 20 and increasing its temperature through resistance heating. Alternatively, the temperature of compression element 20 may be increased by way of magnetic induction, the application of which would be apparent to one of ordinary skill in the art.

Once elongate member 14 is positioned at a desired rotational and axial position relative to coupling element 18, locking element 22 is heated up. It should be understood that locking element 22 is preferably, but not necessarily, heated up substantially concurrently with compression element 20. It should also be understood that locking element 22 is preferably made of a shape-memory material having the same transformation temperature range as that of compression element 20. As discussed above, in one specific embodiment, compression element 20 and the locking element 22 have the same material composition, preferably Nitinol®. As locking element 22 is reformed into its second configuration at a temperature above the transformation temperature range of the shape-memory material, locking element 22 will contract about coupling element 18. As locking element 22 engages and tightens about coupling element 18, side wall 42 will correspondingly compress tightly against connecting portion 38 of elongate member 14. Significant compression forces are developed by locking element 22. These forces are transmitted to side wall 42, which in turn tightly engages connecting portion 38, thereby limiting movement of elongate member 14 relative to coupling element 18.

After locking element 22 is reformed into its second configuration, elongate member 14 will no longer be allowed to freely rotate and translate within channel 48 relative to coupling element 18. Hence, another function of slots 62a, 62b and slots 64a, 64b is to render channel 48 readily collapsible. In other words, as locking element 22 contracts about coupling element 18, the maximum compression force generated by locking element 22 will be applied to the interface between connecting portion 38 and channel 48. Slots 62a, 62b and slots 64a, 64b thus ensure that the recovered stress in locking element 22 will generate the maximum contact pressure between connecting portion 38 and channel 48. As discussed above, locking element 22 is preferably disposed about rounded portions 56 of opposing fingers 54a, 54b adjacent channel 48. This desired positioning also aids in securely clamping connecting portion 38 within channel 48.

Although a preferred embodiment of the present invention contemplates locking element 22 as generating the compression forces necessary to clamp connecting portion 38 within channel 48, it should be understood that, in an alternative embodiment, compression element 20 may be used both to clamp head 28 within inner recess 43 and to clamp connecting portion 38 within channel 48. In this alternative embodiment, compression element 20 generates the required compression forces, and thus locking element 22 is not required.

The present invention provides a spinal fixation system 10 that offers a low profile, multi-axial bone screw assembly. In particular, bone engaging member 12 is connected to elongate member 14 at a location directly beneath elongate member 14. The overall bulk or prominence of the present invention is minimized through the use of coupling device 18 and the utilization of shape-memory technology, in contrast to prior devices which require some form of external nut or cap threaded onto (or into) the top of a receiver member. The present invention also provides a multi-axial bone screw assembly that may be threaded into a vertebral body from the top. In addition, elongate member 14 may be top-loaded, thus greatly simplifying a spinal surgical procedure because elongate member 14 need not be pre-loaded into coupling element 18 prior to insertion into the patient.

To better illustrate the construction of system 10, the dimensions of one manufactured embodiment are hereafter listed. It should be understood, however, that these dimensions are exemplary and are not intended to limit the scope of protection sought. The use of dimensions and tolerances other than those listed are contemplated as within the scope of the invention.

Referring to FIG. 3, shown therein is bone engaging member 12. Bone engaging member 12 is configured for engagement in the lumbar region of the spine and has an overall length of about 54 mm. Spherical head 28, and particularly spherical surface 29, has a diameter of about 7 mm. Annular relief 37 has a diameter of about 5 mm and transitions into threaded shank 35 via a fillet having a radius of 2 mm and an angled surface aligned at about a 45° angle. Threaded shank 35 has a maximum diameter of about 7.5 mm. The overall length of threaded shank 35 is about 45 mm. Tool marks 30, which are disposed about the entire pheriphery of head 28, have a radius of about 0.35 mm and a depth of about 0.05 mm.

Referring to FIGS. 4–7, coupling element 18 has an overall height of about 12.37 mm and an outer diameter $D_1$ of about 8.7 mm. Passage 40 extends generally along longitudinal axis L and has an inner diameter of about 6.78 mm. Inner recess 43 is defined along passage 40 and has a radius of about 1.5 mm. The centerline of inner recess 43 is offset about 1.37 mm from second end 42b. Tapered surface 46 communicates with inner recess 43 at a diameter that is substantially equal to the inner diameter of passage 40, namely about 6.78 mm. Tapered surface 46 extends from inner recess 43 to second end 42b at a distance of about 0.5 mm, as measured along longitudinal axis L. Concave bottom surface 50 of channel 48 has a diameter of about 5.5 mm and has a centerline offset from second end 42*b* at about 7.62 mm. Opposing flat surfaces 52*a*, 52*b* define a channel width $W_1$ of about 5 mm. Rounded portions 56 of opposing fingers 54*a*, 54*b* have a height of about 2 mm and define a maximum outer width $W_2$ therebetween of about 8.7 mm. Rounded portions 56 have a radius of about 1.425 mm. Flat portions 58 of opposing fingers 54*a*, 54*b* are generally flush with opposing flat surfaces 52*a*, 52*b* and define an inner width $W_1$ of about 5 mm. Angled surfaces 60 extend between flat portion 58 and top surface 59 and define a maximum opening between opposing fingers 54*a*, 54*b* of about 6 mm. First and second slots 62*a*, 62*b* each have a width of about 0.5 mm. First slot 62*a* extends from bottom surface 50 of channel 48 toward second end 42*b* and terminates at its closed end in a rounded portion having a radius of about 0.25 mm. The closed end of slot 62*a* is positioned at a minimum distance of about 0.5 mm from second end 42*b*. Second slot 62*b* extends from second end 42*b* toward first end 42*a* and terminates at its closed end in a rounded portion having a radius of about 0.25 mm. The closed end of slot 62*b* is positioned at a minimum distance of about 0.5 mm from the center of concave bottom surface 50. First and second slots 62*a*, 62*b* are aligned generally parallel, and have centerlines which are symmetrical about longitudinal axis L. The distance between the centerline of first slot 62*a* and the centerline of second slot 62*b* is about 1 mm. In other words, narrow section of material 68 is generally aligned along longitudinal axis L and has a width of about 0.5 mm. Slots 64*a*, 64*b* are configured and aligned similar to slots 62*a*, 62*b*. Narrow section of material 70 is configured and aligned similar to section of material 68.

Referring to FIG. 8, compression element 20 has an inner annular surface 76 defining an inner diameter $D_3$ when at a temperature below the transformation temperature range. In this state, inner diameter $D_3$ is slightly greater than outer diameter $D_1$ of coupling element 18, and is preferably about 8.75 mm. When compression element 20 is increased to a temperature above the transformation temperature range, its inner diameter is reduced so that inner annular surface 76' (shown in phantom) may bear against the outer surface of side wall 42 and tightly compress inner recess 43 against head 28. Preferably, the resulting reduced inner diameter $D_3$' is about 8.47 mm. This change in diameter amounts to about a 3% reduction in diameter. This percentage reduction is typical for many medical grade shape-memory alloy materials, including Nitinol®. The outer diameter of compression element 20 is preferably about 11.47 mm and its thickness is preferably about 2 mm.

Referring to FIG. 9, locking element 22 has opposing curved inner surfaces 78 which define an inner width $W_3$ when at a temperature below the transformation temperature range. In this state, inner width $W_3$ is slightly greater than outer width $W_2$ separating rounded portions 56 of opposing fingers 54*a*, 54*b*, and is preferably about 8.75 mm. When locking element 22 is increased to a temperature above the transformation temperature range, flat inner surfaces 80 are shortened so that curved inner surfaces 78' (shown in phantom) may bear against rounded portions 56, and tightly compress concave bottom surface 50 of channel 48 against connecting portion 38 of elongate member 14. Preferably, the resulting reduced inner width $W_3$' is about 8.47 mm. This change in width also amounts to about a 3% reduction in width. The overall length of locking element 22 is preferably about 11.47 mm and the overall width is preferably about 5.85 mm. The thickness of locking element 22 is preferably about 2 mm.

Figure 10:
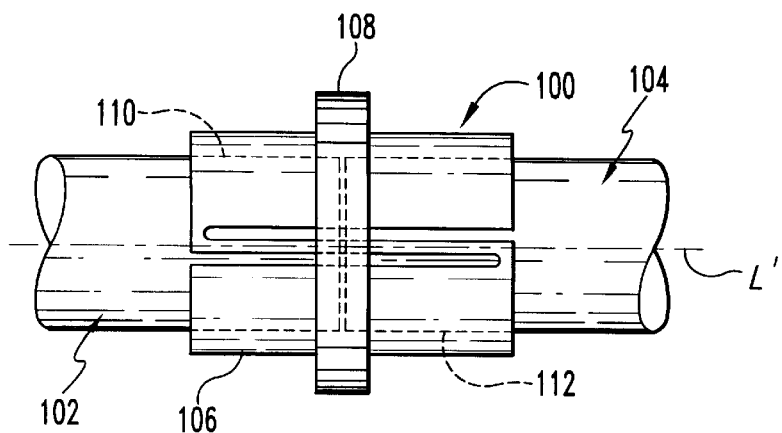
FIG. 10 is a side elevational view of a coupling device according to another embodiment of the present invention.
Figure 11:
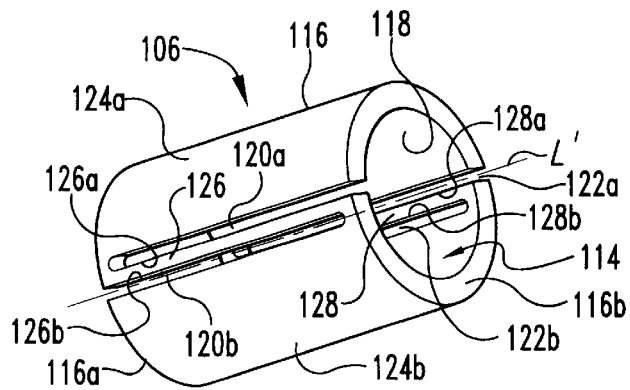
FIG. 11 is a side perspective view of one embodiment of a coupling element used with the device depicted in FIG. 10.
Figure 12:
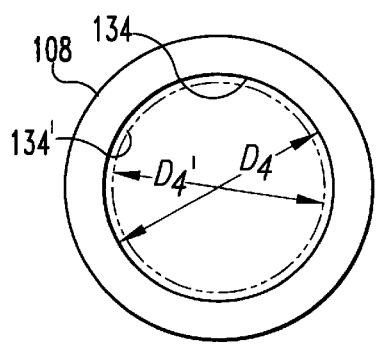
FIG. 12 is a top view of one embodiment of a shape-memory ring used with the device depicted in FIG. 10.

In another embodiment of the present invention, a coupling device 100 is provided as shown in FIGS. 10–12. Coupling device 100 is configured to connect first member 102 to second member 104. Preferably, but not necessarily, first and second members 102, 104 are elongate members. First and second members 102, 104 are preferably spinal rods used in association with a spinal fixation system. However, it should be understood that coupling device 100 can be used in a variety of applications outside of the spinal field.

Referring specifically to FIG. 10, coupling device 100 is shown connecting first member 102 to second member 104. Coupling device 100 includes a coupling element 106 defining a longitudinal axis L' and a compression element 108 disposed about at least a portion of coupling element 106. First member 102 has a connecting portion 110 and second member 104 has a connecting portion 112. Coupling element 106 is configured to connect connecting portion 110 and connecting portion 112 generally along longitudinal axis L'. Preferably, but not necessarily, connecting portions 110, 112 of first and second members 102, 104 have generally circular outer cross sections. However, it should be understood that connecting portions 110, 112 can also take on a variety of alternative shapes, such as, for example, a square, an ellipse, or a number of other polygonal configurations.

Referring now to FIG. 11, shown therein are various structural details of coupling element 106. Coupling element 106 includes a passage 114 extending therethrough generally along longitudinal axis L'. Preferably, but not necessarily, coupling element 106 is substantially cylindrical-shaped. Passage 114 is bounded by a side wall 116 having a first end 116*a* and an opposing second end 116*b*. Side wall 116 defines an inner surface 118 having an inner diameter slightly greater than the outer diameter of connecting portions 110, 112 of first and second members 102, 104. Preferably, but not necessarily, inner surface 118 has a constant inner diameter between first end 116*a* and second end 116*b*. Side wall 116 defines a first slot 120*a* and a second slot 120*b*. First slot 120*a* extends from second end 116*b* toward first end 116*a*. Second slot 120*b* extends from first end 116*a* towards second end 116*b*. A portion of second slot 120*b* is positioned proximately adjacent and longitudinally overlapping a portion of first slot 120*a*. Preferably, but not necessarily, first slot 120*a* terminates at a location proximately adjacent first end 116*a*. Similarly, second slot 120*b* preferably terminates at a location proximately adjacent second end 116*b*.

First slot 120*a* and second slot 120*b* are preferably aligned substantially parallel to one another. However, it should be understood that first and second slots 120*a*, 120*b* may alternatively be aligned in a non-parallel configuration. It should also be understood that slots 120*a*, 120*b* need not necessarily be straight, but can take on angled or curved configurations as well. In a preferred embodiment of coupling element 106, first and second slots 120*a*, 120*b* are aligned substantially parallel to one another and aligned generally along longitudinal axis L'. Preferably, but not necessarily, side wall 116 defines a second pair of slots 122*a*, 122*b*, configured substantially similar to first and second slots 120*a*, 120*b*. Second pair of slots 122*a*, 122*b* is positioned generally opposite first and second slots 120*a*, 120*b*. In other words, second pair of slots 122*a*, 122*b* is positioned in diametric opposition relative to first and second slots 120*a*, 120*b*.

Coupling element 106 is thus comprised of two integrally formed longitudinal segments 124*a*, 124*b*. Segments 124*a*, 124*b* define passage 114 and are connected by generally opposing narrow sections of material 126, 128. Section 126 has first and second edges 126*a*, 126*b* which preferably extend generally along longitudinal axis L'. Section 128 has first and second edges 128a, 128b which also preferably extend generally along longitudinal axis L'. Although first and second edges 126a, 126b are shown to be aligned substantially parallel, it should be understood that they may alternatively be aligned in a non-parallel configuration. Additionally, although first and second edges 126, 126b are shown aligned generally along longitudinal axis L', it should be understood that either one or both of edges 126a, 126b may be aligned transverse to longitudinal axis L'. It should also be understood that although edges 126a, 126b are illustrated as being generally straight, they may alternatively take on other configurations, such as angled or curved. Similarly, first and second edges 128a, 128b of section 128 can take on any of the configurations described immediately above regarding edges 126a, 126b. Moreover, although the preferred embodiment contemplates segments 126, 128 as being generally symmetrical (i.e., configured as longitudinal halves), it should be understood that segments 126, 128 can alternatively take on non-symmetrical configurations as well. In other words, narrow section of material 126 does not necessarily have to be positioned in diametric opposition to narrow section of material 128.

Figure 11A:
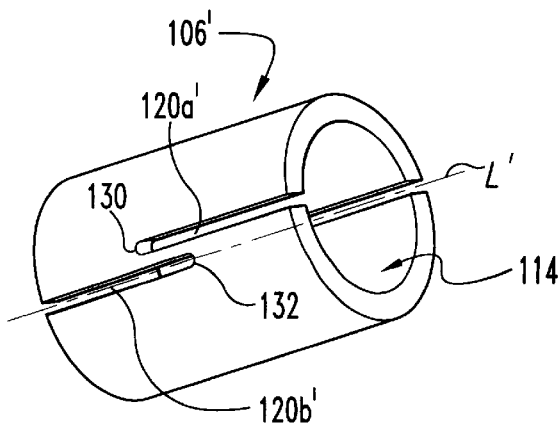
FIG. 11a is a side perspective view of another embodiment of a coupling element used with the device depicted in FIG. 10.

Referring now to FIG. 11a, shown therein is coupling element 106', an alternative embodiment of a coupling element which may be used in association with coupling device 100. In many ways, coupling element 106' is configured similarly to coupling element 106. However coupling element 106' includes a first slot 120a' and a second slot 120b' in which only a relatively small portion of second slot 120b' is positioned proximately adjacent and longitudinally overlapping a relatively small portion of first slot 120a'. In other words, first slot 120a' terminates in a closed end portion 130 and second slot 120b' terminates in a closed end portion 132, with closed end portion 130 positioned proximately adjacent and longitudinally overlapping closed end portion 132. In a preferred embodiment, the lengths of first slot 120a' and second slot 120b' are approximately equal. In other words, closed end portion 130 and closed end portion 132 longitudinally overlap at about the center of coupling element 106', as measured along the length of longitudinal axis L'. However, it should be understood that first and second slots 120a', 120b' may define different lengths. In other words, closed end portion 130 and closed end portion 132 may longitudinally overlap at a location anywhere along longitudinal axis L'.

Referring now to FIG. 12, shown therein is compression element 108. Compression element 108 is at least partially formed of a shape-memory material such as, for example, Nitinol®. Compression element 108 is generally ring-shaped and defines an inner diameter $D_4$. It should be understood that while compression element 106 is depicted as a circular ring, other shapes and configurations are also contemplated as would occur to one of ordinary skill in the art.

When the shape-memory material within compression element 108 is in its martensitic or room temperature state, inner diameter $D_4$ is slightly greater than the outer diameter of coupling element 106. In other words, compression element 108 includes an inner annular surface 134 that preferably corresponds to the outer surface of side wall 116, such that compression element 106 can be easily slid over side wall 116 when the shape-memory material is at a temperature below its transformation temperature range. In this martensitic state, first member 102 and second member 104 will be allowed to freely rotate and translate within passage 114 relative to coupling element 106.

Once first and second members 102, 104 are positioned at a desired rotational orientation and axial position relative to longitudinal axis L', the shape-memory material within compression member 108 is heated up. As the temperature of the shape-memory material is increased beyond the transformation temperature range, the shape-memory material shifts from its martensitic state to its austenitic state. In the austenitic state, compression element 106 is reformed into a second configuration in which its inner diameter is reduced to $D_4'$, as reflected by inner annular surface 134' (shown in phantom). As compression element 108 is reformed into its second configuration, it will contract about coupling element 106. As compression element 108 engages and tightens about coupling element 106, side wall 116 will correspondingly compress tightly against connecting portion 110 of first member 102 and connecting portion 112 of second member 104. The compression forces developed by compression element 108 are transmitted to side wall 116, which in turn tightly engages connecting portions 110, 112, thereby limiting movement of first member 102 and second member 104 relative to coupling element 106.

Thus, after compression element 108 is reformed into its second configuration, first and second members 102, 104 will no longer be allowed to freely rotate and translate within passage 114 relative to longitudinal axis L'. Hence, one function of slots 120a, 120b and slots 122a, 122b is to render passage 114 readily collapsible. Thus, as compression element 108 contracts about coupling element 106, the maximum compression force generated by compression element 108 will be applied to the interface between inner surface 118 of side wall 116 and the outer surfaces of connecting portions 110, 112. This ensures that the recovered stress in compression element 108 will generate the maximum contact pressure between inner surface 118 and connecting portions 110, 112. Preferably, compression element 108 is centered along the length of coupling element 106 and overlaps at least a portion of the longitudinally overlapping portions of slots 120a, 120b and slots 122a, 122b. However, it should be understood that compression element 108 can be positioned at any location along the length of coupling element 106.

Figure 13:
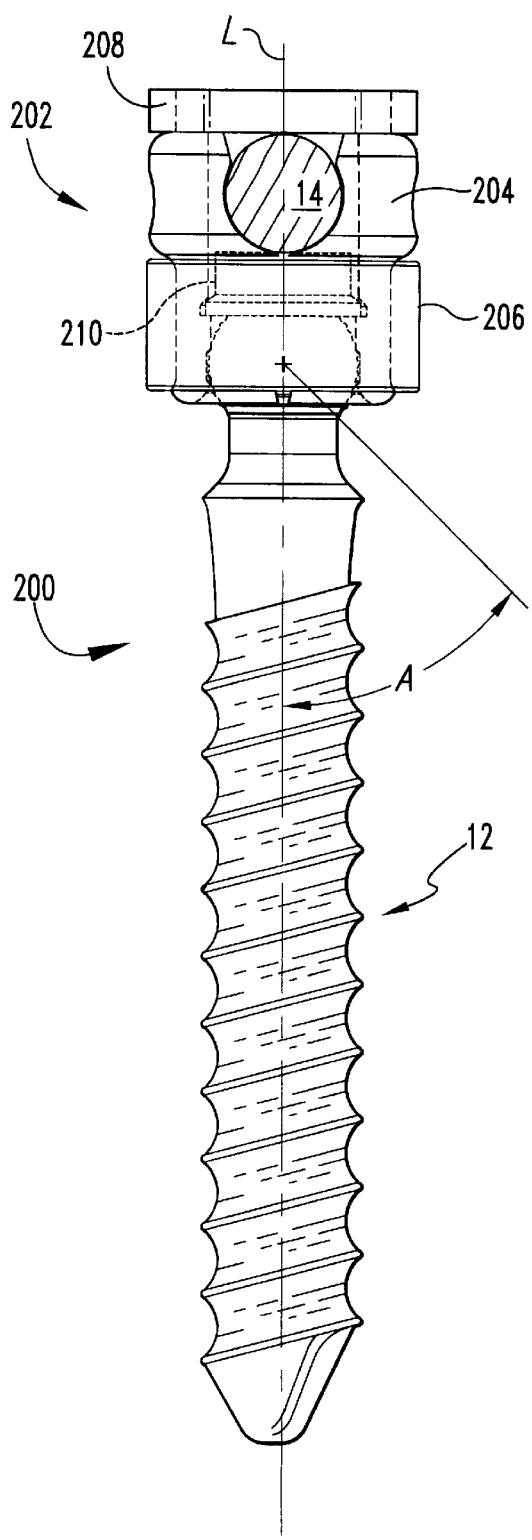
FIG. 13 is an elevation view of a spinal fixation system according to another embodiment of the present invention.

FIG. 13 depicts a spinal fixation system 200 according to another embodiment of the present invention. Similar to spinal fixation system 10, system 200 includes a bone engaging member 12 and an elongate member 14. A coupling device 202 is provided for connecting bone engaging member 12 to elongate member 14. As the particular structural features and applications of bone engaging member 12 and elongate member 14 have already been described in detail above with regard to spinal fixation system 10, they will not hereinafter be discussed with regard to system 200. Additionally, it should be understood that system 200 may be used in any application in which system 10 is used, including, but not limited to, the particular applications of system 10 discussed above.

Figure 14:
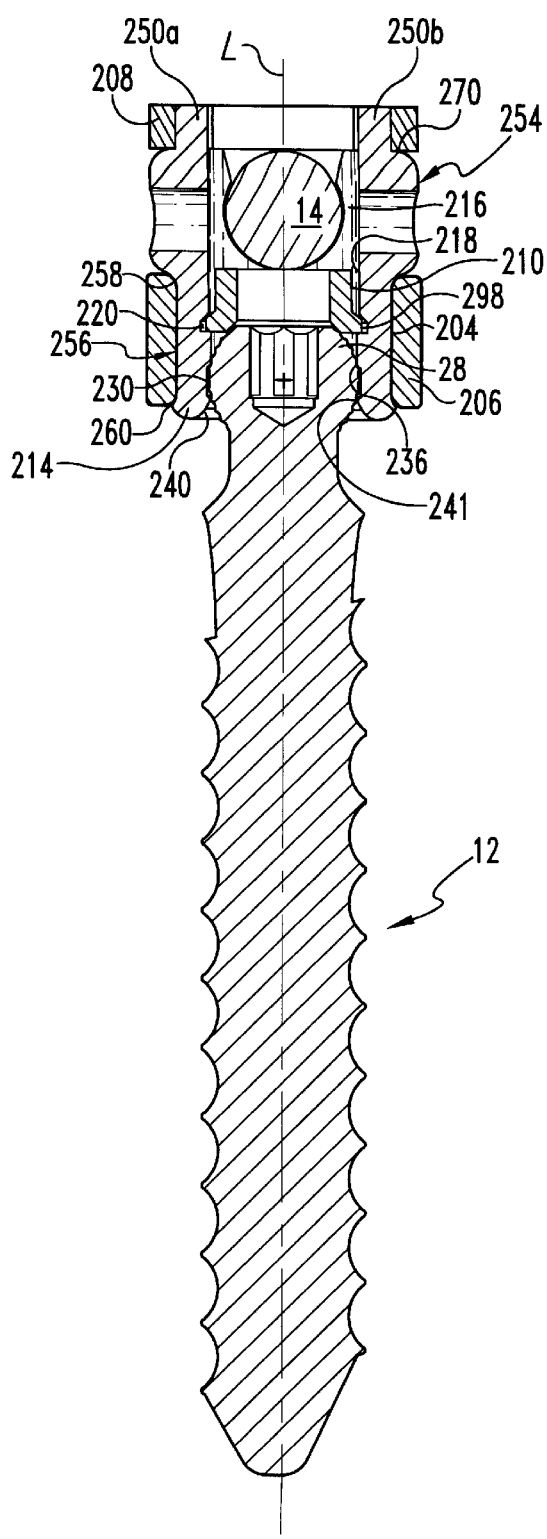
FIG. 14 is a cross-sectional view of the system depicted in FIG. 13.

Referring now to FIGS. 13 and 14, bone engaging member 12 is shown connected to elongate member 14 by way of coupling device 202. In a preferred embodiment, coupling device 202 includes a coupling element 204 defining a longitudinal axis L, a compression element 206, a locking element 208, and a blocking member 210. Coupling element 206 is configured to receive a portion of bone engaging member 12 and elongate member 14 therein. Compression element 206 and the locking element 208 are disposed about portions of coupling element 204 and aligned generally along longitudinal axis L. Blocking member 210 is disposed within coupling element 206 and aligned generally along longitudinal axis L.

Bone engaging member 12 is capable of assuming a wide range of angles, up to angle A, relative to longitudinal axis L. Although angle A is illustrated in FIG. 13 as lying in a single plane, it should be understood that bone engaging member 12 is capable of pivoting through a generally cone-shaped path relative to longitudinal axis L. In one working configuration of coupling device 202, bone engaging member 12 is allowed to freely rotate and pivot relative to coupling element 204, and in another working configuration, coupling element 204 is compressed against a portion of bone engaging member 12, thereby limiting movement of bone engaging member 12 relative to coupling element 204. Similarly, in one working configuration of coupling device 202, elongate member 14 is allowed to rotate and translate relative to coupling element 204, and in another working configuration, coupling element 204 is compressed against a portion of elongate member 14, thereby limiting movement of elongate member 14 relative to coupling element 204.

Figure 15:
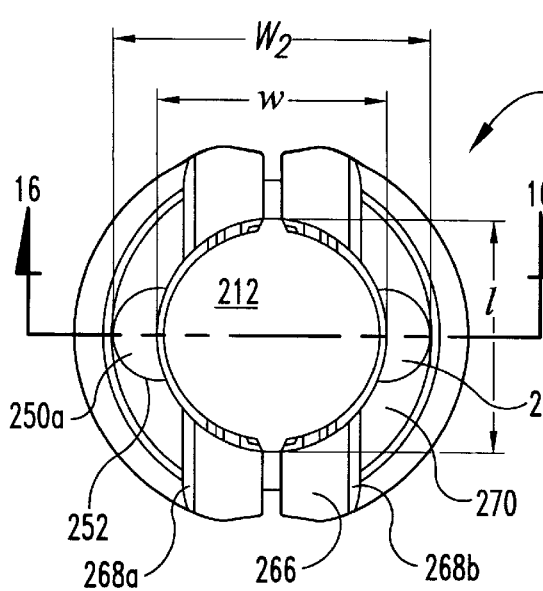
FIG. 15 is a top view of one embodiment of a coupling element used with the system depicted in FIG. 13.
Figure 16:
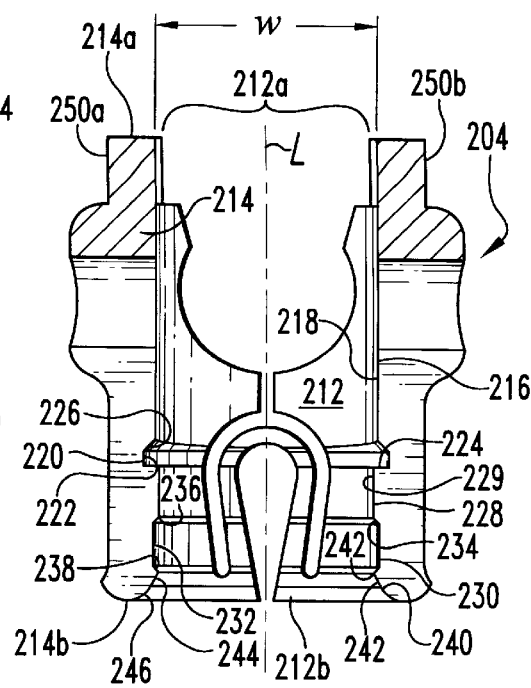
FIG. 16 is a side cross-sectional view of the coupling element shown in FIG. 15 taken along line 16—16 of FIG. 15.

Referring now to FIGS. 15–18, shown therein are various structural details of coupling element 204. Referring specifically to FIG. 16, coupling element 204 includes a passage 212 extending therethrough generally along longitudinal axis L, thus defining an upper opening 212a and a lower opening 212b. Longitudinal passage 212 is bounded by a side wall 214 having a first end 214a and an opposing second end 214b. Longitudinal passage 212 is partially comprised of an oblong slot 216, extending from first end 214a toward second end 214b. Slot 216 has an inner surface 218 defining a width w and a length l (FIG. 15). In one embodiment, length l is only slightly greater than width w. Longitudinal passage 212 also includes a radial groove 220 disposed adjacent the end of slot 216. Radial groove 220 defines a circumferential surface 222, an annular surface 224, and a peripheral angular surface 226 serving as a transition between inner surface 218 of slot 216 and circumferential surface 222. A generally circular bore 228, defining an inner surface 229, extends from radial groove 220 toward second end 214b. Bore 228 transitions into a radial recess 230. Radial recess 230 includes a circumferential surface 232, an upper peripheral angular surface 234, and a lower peripheral angular surface 238. Angular surface 234 serves as a transition between inner surface 229 of circular bore 228 and circumferential surface 232. The point at which angular surface 234 intersects inner surface 229 defines a circular upper edge 236. Similarly, lower peripheral angular surface 238 transitions into a conical bore 240 so as to define a circular lower edge 241. Conical bore 240 has an outwardly tapering inner surface 242 extending between angular surface 238 and second end 214b. Preferably, but not necessarily, inner surface 242 includes a generally flat angular surface 244 extending outwardly from angular surface 238 and transitioning into an outwardly extending arcuate surface 246, which in turn transitions into second end 214b. Although longitudinal passage 212 has been described as having a generally circular or oblong inner cross section, other shapes are also contemplated as being within the scope of the invention.

Referring once again to FIG. 14, it can be seen that head 28 of bone engaging member 12 is received within radial recess 230 of coupling element 204 such that the angular alignment of bone engaging member 12 may be variably adjusted relative to longitudinal axis L. In a preferred embodiment, only circular upper and lower edges 236, 241 contact head 28 when head 28 is disposed within radial recess 230. Additionally, it can be seen that outwardly tapering conical bore 240 provides an enhanced range of movement of bone engaging member 12 relative to coupling element 204 as spherical head 28 is pivotally rotated relative to radial recess 230. Conical bore 240 is configured to permit bone engaging member 12 to be rotated up to angle A relative to longitudinal axis L. In accordance with a preferred embodiment, circular upper and lower edges 236, 241 have a diameter that is slightly less than the outer diameter of head 28. In this manner, in order for head 28 to be received within radial recess 230, side wall 214 must be slightly outwardly deformed to expand longitudinal passage 212 to a size sufficient to accept head 28 within radial recess 230. Once head 28 is positioned within radial recess 230, side wall 214 is allowed to snap back into its original, undeformed state. The elastic characteristics of coupling element 204 thus provisionally maintain head 28 within radial recess 230.

Referring collectively to FIGS. 15–18, it can be seen that side wall 214 defines a pair of opposing fingers 250a, 250b projecting generally in a longitudinal direction. Each of fingers 250a. 250b includes a rounded outer portion 252 facing outwardly relative to longitudinal passage 212 and defining an outer width $W_2$ (FIG. 15). Fingers 250a, 250b extend from a cylindrical-shaped upper portion 254 having an outer diameter slightly larger than width $W_2$. The upper and lower edges of upper portion 254 are preferably, but not necessarily, rounded to avoid sharp edges which may potentially damage adjacent tissue. Coupling element 204 also includes a cylindrical-shaped lower portion 256 extending from upper portion 254 in a longitudinal direction. Lower portion 256 has an outer diameter $D_1$ (FIG. 17) that is preferably, but not necessarily, substantially equal to width $W_2$. Preferably, the transition between upper portion 254 and lower portion 256 defines a circular fillet 258. The end of lower portion 256 opposite circular fillet 258 defines an outward projection 260. Preferably, the transition between lower portion 256 and outward projection 260 defines a circular fillet 262. The lower edge of outer projection 260 is preferably, but not necessarily, rounded to avoid a sharp edge which may potentially damage adjacent tissue. Although coupling element 204 has been described as having a generally circular outer cross section, other shapes are also contemplated as being within the scope of the invention.

Figure 17:
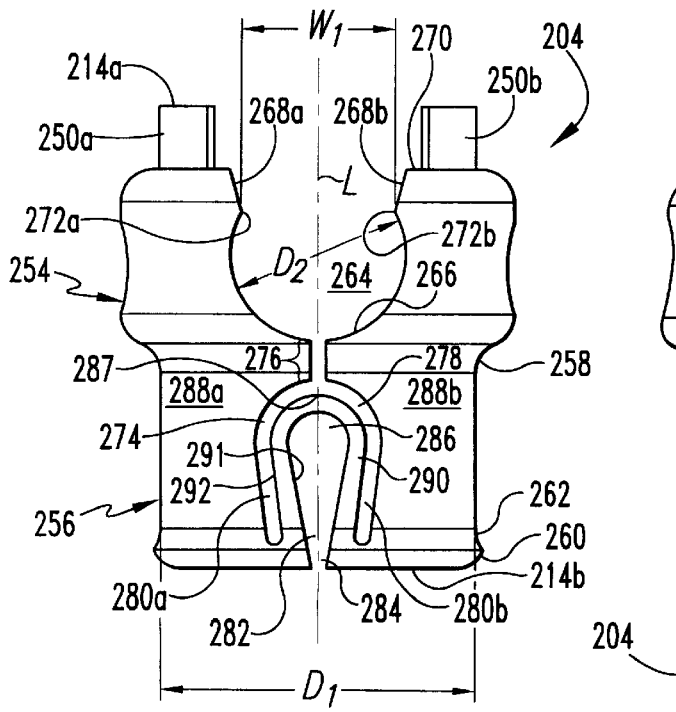
FIG. 17 is a side elevation view of the coupling element shown in FIG. 15.

Referring specifically to FIG. 17, it can be seen that upper portion 254 of coupling element 204 defines a channel 264 extending laterally therethrough. Channel 264 intersects longitudinal passage 212 and is preferably aligned generally perpendicular to longitudinal axis L. Channel 264 is bounded by a concave bottom surface 266 and opposing angular surfaces 268a, 268b extending outwardly from bottom surface 266 to the upper surface 270 of upper portion 254. The intersection of angular surfaces 268a, 268b with bottom surface 266 defines transverse edges 272a, 272b. One purpose of angular surfaces 268a, 268b is to aid in guiding elongate member 14 into channel 264. Concave bottom surface 266 has a channel diameter $D_2$ that is preferably substantially equal to the outer diameter of connecting portion 38 of elongate member 14. Opposing transverse edges 272a, 272b define a channel width $W_1$ (FIG. 17) that is preferably slightly smaller than the outer diameter of connecting portion 38. Elongate member 14 is received within channel 264 by sliding elongate member 14 through channel 264 along concave bottom surface 266 in a direction transverse to longitudinal axis L. Alternatively, elongate member 14 may be slid between opposing angular surfaces 268a, 268b and slightly deforming side wall 214 so that opposing transverse edges 272a, 272b are splayed apart far enough to accept elongate member 14 therebetween. Elongate member 14 can then be transferred along longitudinal axis L toward concave bottom surface 266. Once elongate member 14 is positioned adjacent concave bottom surface 266, side wall 214 is allowed to snap back into its original, undeformed state. In this manner elongate member 14 is provisionally maintained within channel 264. However, it should be understood that channel diameter $D_2$ and channel width $W_2$ can alternatively be substantially equal.

Side wall 214 of coupling element 204 defines a first slot 274, extending from channel 264 toward second end 214b. First slot 274 includes a base portion 276, extending from channel 264 and transitioning into a forked portion 278. Base portion 276 extends generally along longitudinal axis L. Forked portion 278 defines a first prong 280a and a second prong 280b. Preferably, first and second prongs 280a, 280b are generally symmetrical relative to longitudinal axis L so as to generally define a U-shape. First and second prongs 280a, 280b have a slight inward taper as they extend toward second end 214b. Side wall 214 also defines a second slot 282, extending from second end 214b toward first end 214a generally along longitudinal axis L. Second slot 282 includes a narrow end 284, extending from second end 214b and outwardly transitioning into a wide end 286 so as to generally define a tear drop shape. Second slot 282 is substantially aligned with base portion 276 of first slot 274 so as to position second slot 282 between opposing first and second prongs 280a, 280b. Thus, it can be seen that a portion of second slot 282 is positioned proximately adjacent and longitudinally overlapping a portion of first slot 274. In other words, a plane aligned perpendicular to longitudinal axis L and positioned at a select location along longitudinal axis L would intersect both first slot 274 and second slot 282. Preferably, but not necessarily, prongs 280a, 280b of first slot 274 terminate at a location proximately adjacent second end 214b. Additionally, wide end 286 of second slot 282 preferably terminates at a location proximately adjacent the inner base 287 of forked portion 278 of first slot 274. However, it should be understood that only a relatively small portion of first slot 274 need necessarily be positioned proximately adjacent and longitudinally overlapping second slot 282.

Although prongs 280a, 280b of first slot 274 preferably have a slight inward taper, it should be understood that prongs 280a, 280b may alternatively be aligned in a parallel configuration. It should also be understood that prongs 280a, 280b need not necessarily be straight, but can take on angled or curved configurations as well. Although second slot 282 has a tear drop shape, it should be understood that second slot 282 can take on alternative configurations. Additionally, in the illustrated embodiment, first slot 274 can be said to extend from first end 214a if first slot 274 is defined to include channel 264 and the space between opposing fingers 250a, 250b. In other words, channel 264 and the space between opposing fingers 250a, 250b can be considered to be part of first slot 274. However, it should be understood that first slot 274 may alternatively be positioned along side wall 214 without intersecting channel 264, while still extending from first end 214a.

Preferably, side wall 214 defines a second pair of slots (not shown) configured substantially similar to and positioned diametrically opposite first and second slots 274, 282. However, it should be understood that the second pair of slots can take on configurations or positions different from those of first and second slots 274, 282. It can thus be seen that coupling element 204 is comprised of two integrally formed longitudinal segments 288a, 288b, which are connected by narrow sections of material 290. Narrow section of material 290 is generally U-shaped, corresponding to the shape of forked portion 278 of first slot 274. Section of material 290 has an inner edge 291 which defines second slot 282, and an outer edge 292 which partially defines first slot 274. Although section of material 290 is generally U-shaped, it should be understood that section of material 290 can alternatively take on other shapes or configurations. Moreover, although a preferred embodiment contemplates longitudinal segments 288a, 288b as being generally symmetrical (i.e., configured as longitudinal halves), it should be understood that segments 288a, 288b can alternatively take on non-symmetrical configurations as well.

Figure 18:
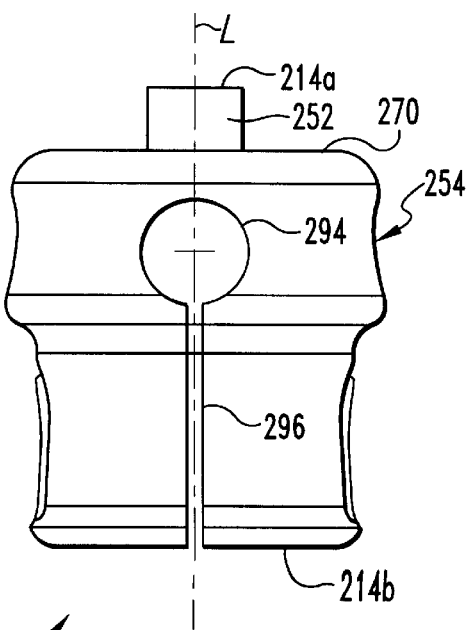
FIG. 18 is an end elevation view of the coupling element shown in FIG. 15.
Figure 21:
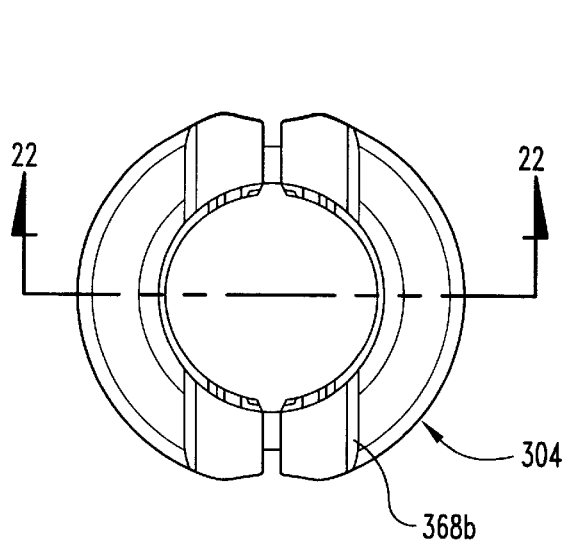
FIG. 21 is a top view of one embodiment of the coupling element used with the system depicted in FIG. 19.

Referring to FIG. 18, upper portion 254 defines a generally circular bore 294, extending through side wall 214 and intersecting longitudinal passage 212. Preferably, circular bore 294 is aligned generally perpendicular to longitudinal axis L and positionally offset by 90° relative to channel 264. A longitudinal slot 296 passes through side wall 214, extending from second end 214b and intersecting circular bore 294. Preferably, but not necessarily, slot 296 is straight and extends generally along longitudinal axis L.

Referring once again to FIGS. 13 and 14, it can be seen that compression element 206 and locking element 208 are disposed about a portion of coupling element 204, and are each aligned generally along longitudinal axis L. More specifically, compression element 206 is disposed about lower portion 256 and positioned between circular fillet 258 and outward projection 260. Locking element 208 is disposed about opposing fingers 250a, 250b and positioned adjacent upper surface 270 of upper portion 254. Similar to compression element 20 and locking element 22 of spinal fixation system 10, compression element 206 and locking element 208 are at least partially formed of a shape-memory material such as, for example, Nitinol®. Compression element 206 is generally ring-shaped and is configured substantially similar to compression element 20 (shown in FIG. 8 and discussed in detail above). Although compression element 206 is illustrated as having a thickness substantially equal to the distance between circular fillet 258 and outward projection 260, it should be understood that a plurality of compression elements 206 can alternatively be positioned about lower portion 256, each having a thickness approximately equal to the thickness of compression element 20. Locking element 208 is in the shape of an oblong ring and has a configuration substantially similar to locking element 22 (shown in FIG. 9 and described in detail above). Because the application and operation of compression element 206 and locking element 208 are substantially identical to that of compression element 20 and locking element 22, respectively, they will not be discussed hereinafter.

Blocking member 210 is shown positioned within longitudinal passage 212, and more specifically within oblong slot 216. Blocking member 210 has a generally cylindrical shape, and includes a peripheral, radial segment 298 having a shape substantially corresponding to the shape of radial groove 220 of coupling element 204. The structural features, application, and operation of blocking member 210 is fully described in U.S. patent application Ser. No. 09/407,431, entitled "Device and Method for Selectively Preventing the Locking of a Shape-Memory Alloy Coupling System" and filed on the same day as the present application, which is hereinafter incorporated by reference into the present application.

In an initial state, blocking member 210 is positioned within slot 216 with the outer surface of radial segment 298 abutting a portion of inner surface 218 of slot 216. In this initial state, as the shape-memory material within compression element 206 and locking element 208 is heated up above its transformation temperature range, blocking member 210 will absorb the compressive forces exerted by compression element 206 and locking element 208 to thereby prevent bone engaging member 12 and elongate member 14 from being locked into position relative to coupling element 204. However, when blocking member 210 is in a second state, with radial segment 298 positioned within radial groove 220, the compressive forces generated by compression element 206 and locking element 208 will be directly applied to coupling element 204, thus resulting in the clamping of bone engaging member 12 and elongate member 14 into a desired position relative to coupling element 204.

From the above discussion, it should be apparent that one finction of first and second slots 274, 282 is to render longitudinal passage 212 readily collapsible. As compression element 206 contracts about coupling element 204, the maximum compressive force generated by compression element 204 will be applied to the interface between head 28 of bone engaging member 12 and upper and lower edges 236, 241 of radial recess 230. First and second slots 274, 282 thus ensure that the recovered stress in compression element 206 will generate the maximum contact pressure between head 28 and upper and lower edges 236, 241 so as to securely clamp bone engaging member 10 within radial recess 230. Similarly, circular bore 294 and longitudinal slot 296 also aid in rendering longitudinal passage 212 readily collapsible so as to further aid in recovering the maximum compressive force generated by compression element 206. Another function of first and second slots 274, 282 is to render channel 264 readily collapsible. As locking element 208 contracts about opposing fingers 250a, 250b, the maximum compressive force generated by locking element 208 will be applied to the interface between connecting portion 38 of elongate member 14 and the concave bottom surface 266 of channel 264. First and second slots 274, 282 thus ensure that the recovered stress in locking element 208 will generate the maximum contact pressure between connecting portion 38 and concave bottom surface 266 so as to securely clamp elongate member 14 within channel 264.

FIGS. 19 and 20 depict a spinal fixation system 300 according to yet another embodiment of the present invention. Spinal fixation system 300 is similar to system 200 in that it includes a bone engaging member 12, an elongate member 14, and a coupling device 302 for connecting bone engaging member 12 to elongate member 14. It should be understood that system 300 may be used in any application in which system 200 is used. In a preferred embodiment, coupling device 302 includes a coupling element 304 defining a longitudinal axis L, a compression element 306, and a blocking member 310. Compression element 306 is disposed about a portion of coupling element 304 and aligned generally along longitudinal axis L. Blocking member 310 is disposed within coupling element 306 and aligned generally along longitudinal axis L.

Figure 22:
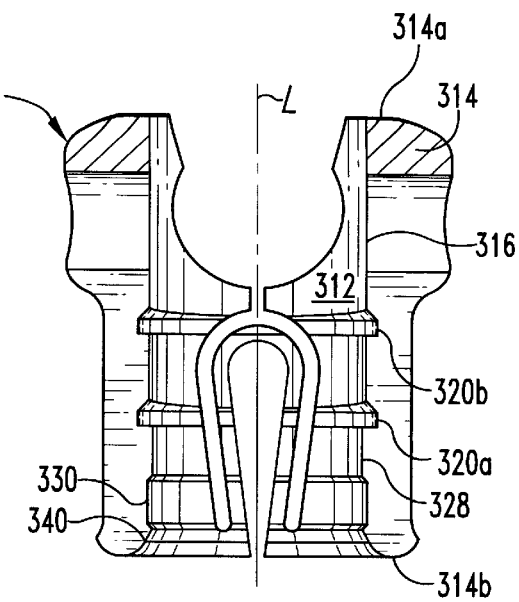
FIG. 22 is a side cross-sectional view of the coupling element shown in FIG. 21 taken along line 22—22 of FIG. 21.

Referring now to FIGS. 21–24, shown therein are various structural details of coupling element 304. Referring specifically to FIG. 22, coupling element 304 includes a passage 312 extending therethrough generally along longitudinal axis L. Longitudinal passage 312 is bounded by a side wall 314, having a first end 314a and an opposing second end 314b, and is configured similar to longitudinal passage 212 of coupling element 204. Specifically, passage 312 includes an oblong slot 316 configured similar to slot 216, a first radial groove 320a configured similar to radial groove 220, a circular bore 328 configured similar to bore 228, a radial recess 330 configured similar to radial recess 230, and a conical bore 340 configured similar to bore 240. The only significant difference between longitudinal passage 312 and longitudinal passage 212 is that longitudinal passage 312 includes a second radial groove 320b disposed along slot 316 between first end 314a and first radial groove 320a.

Referring once again to FIGS. 21–24 collectively, coupling element 304 includes a cylindrical-shaped upper portion 354 and a cylindrical-shaped lower portion 356 extending from upper portion 354 in a longitudinal direction. Lower portion 356 has an outer diameter $D_1$ that is preferably, but not necessarily, less than the outer diameter of upper portion 354. The transition between upper portion 354 and lower portion 356 defines a circular fillet 358. The end of lower portion 356 opposite circular fillet 358 defines an outward projection 360. The transition between lower portion 356 and outward projection 360 defines a circular fillet 362. Thus, it can be seen that the outer cross section of coupling element 304 is configured substantially similar to that of coupling element 204, with the exception that coupling element 304 does not include a pair of opposing longitudinal fingers extending from upper portion 354.

Figure 23:
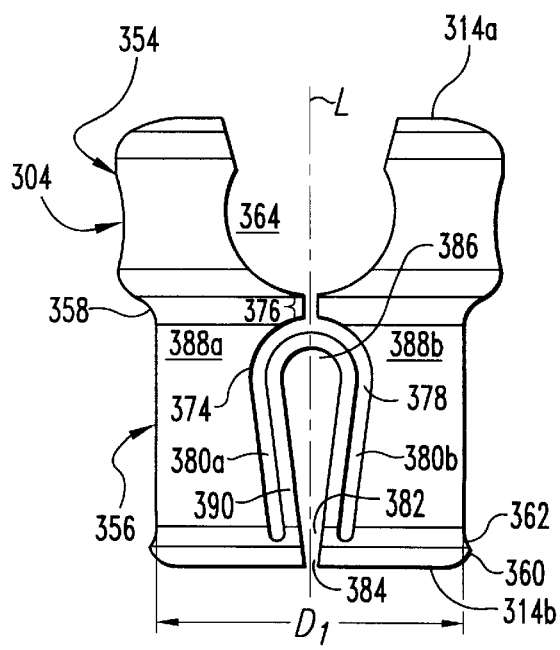
FIG. 23 is a side elevational view of the coupling element shown in FIG. 21.

Referring specifically to FIG. 23, it can be seen that upper portion 354 is configured substantially similar to upper portion 254 of coupling element 204. Specifically, upper portion 354 includes a channel 364 extending laterally therethrough, intersecting longitudinal passage 312 and aligned generally perpendicular to longitudinal axis L. Channel 364 is configured similar to channel 264 of coupling element 204, and therefore will not be described hereinafter. Elongate member 14 is received within channel 364 in a manner similar to that described above with regard to coupling element 204.

Side wall 314 of coupling element 304 defines a first slot 374, extending from channel 364 toward second end 314b. First slot 374 is configured substantially similar to slot 274 of coupling element 204, including a base portion 376 transitioning into a forked portion 378. Fork portion 378 defines first and second prongs 380a, 380b which are generally symmetrical relative to longitudinal axis L so as to generally define a U-shape. The only significant differences between first slot 374 and first slot 274 of coupling element 204 is that base portion 376 has a length slightly less than that of base portion 276, and first and second prongs 380a, 380b have a length slightly greater than that of first and second prongs 280a, 280b due to the increased length of lower portion 354 relative to lower portion 254. Side wall 314 also defines a second slot 382, configured similar to second slot 282 of coupling element 204, including a narrow end 384 transitioning into a wide end 386 so as to define a tear drop shape. Second slot 382 is substantially aligned with base portion 376 of first slot 374 so as to position second slot 382 between opposing first and second prongs 380a, 380b. Thus, it can be seen that a portion of second slot 382 is positioned proximately adjacent and longitudinally overlapping a portion of first slot 374.

Preferably, side wall 314 defines a second pair of slots (not shown) configured substantially similar to and positioned diametrically opposite first and second slots 374, 382. It can thus be seen that coupling element 304 is comprised of two integrally formed longitudinal segments 388a, 388b which are connected by narrow sections of material 390 configured substantially similar to narrow sections of material 290 of coupling element 204.

Figure 24:
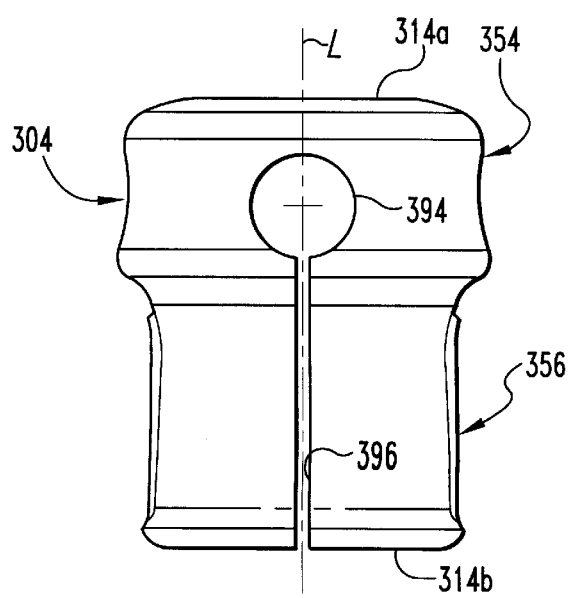
FIG. 24 is an end elevation view of the coupling element shown in FIG. 21.

Referring to FIG. 24, upper portion 354 defines a generally circular bore 394, extending through side wall 314 and intersecting longitudinal passage 312. Preferably, circular bore 394 is aligned generally perpendicular to longitudinal axis L and positionally offset by 90° relative to channel 364. A longitudinal slot 396 passes through side wall 314, extending from second end 314b and intersecting circular bore 394. Preferably, but not necessarily, slot 396 is straight and extends generally along longitudinal axis L.

Referring once again to FIGS. 19 and 20, it can be seen that compression element 306 is disposed about a portion of coupling element 304 and generally aligned along longitudinal axis L. More specifically, compression element 306 is disposed about lower portion 356 and positioned between circular fillet 358 and outward projection 360. Blocking member 310 is shown positioned within longitudinal passage 312, and more specifically within oblong slot 316. Blocking member 310 is configured similar to blocking member 210, except that blocking element 310 includes a pair of radial segments 398a, 398b having shapes substantially corresponding to the shapes of radial grooves 320a, 320b, respectively. The application and operation of blocking member 310 is substantially similar to that of blocking member 210, and will thus not be discussed hereinafter.

It should thus be apparent that one function of first and second slots 374, 382 is to render longitudinal passage 312 readily collapsible so as to securely clamp bone engaging member 10 within radial recess 330. Similarly, bore 394 and longitudinal slot 396 also aid in rendering longitudinal passage 312 readily collapsible so as to further aid in recovering the maximum compressive force generated by compression element 306. Another function of first and second slots 374, 382 is to render channel 364 readily collapsible so as to securely clamp elongate member 14 within channel 364. Unlike coupling device 202, which includes a locking element 208 to provide additional compressive force, coupling device 302 relies solely on compression element 306 to provide the requisite compressive forces required to securely clamp bone engaging member 12 and elongate member 14 in position relative to coupling element 304. Thus, it should be appreciated that this particular configuration of coupling device 302 does not require a separate locking element.

While the invention has been illustrated and described in detail in the drawings and foregoing description, the same is to be considered as illustrative and not restrictive in character, it being understood that only the preferred embodiments have been shown and described, and that all changes and modifications that come within the spirit of the invention are desired to be protected.

For example, while the preferred embodiment of systems 10, 200, and 300 contemplates the inclusion of a bone screw, such as bone engaging member 12, other bone engaging members are also contemplated. For example, the multi-axial capabilities of systems 10, 200, and 300 are equally applicable to a vertebral hook. Similarly, while the preferred embodiment of coupling device 100 contemplates the connection of two elongate members, such as spinal rods, coupling device 100 can alternatively be used to connect first and second members having various configurations as would occur to one having ordinary skill in the art to which the invention relates. Additionally, coupling device 100 can be used to connect members having an application outside of the spinal field. Furthermore, the components of systems 10, 200, and 300 may be correspondingly sized according to the portion of the spine within which the particular assembly is to be used. For instance, treatment of the lumbar region of the spine may require components which are sized somewhat larger than components used to treat the thoracic or cervical regions of the spine.

Additionally, the shape-memory material within systems 10, 200 and 300, and more particularly within the compression and locking elements, could be tailored to exhibit stress-induced martensite characteristics. Importantly, such use of stress-induced martensite would not require a corresponding change in temperature to effect reformation of the compression and locking elements toward their original, memorized configurations. The shape-memory material would remain in a stress-induced martensitic state while the compression and locking elements are maintained in their first configuration, and at least a portion of the shape-memory material would be transformed to an austenitic state during reformation of the compression and locking elements toward their second, memorized configurations. Further details regarding the use and characteristics of stress-induced martensite are more fully described in U.S. Pat. No. 5,597,378 to Jervis, entitled "Medical Devices Incorporating SIM Alloy Elements", which is hereinafter incorporated by reference into the subject application.

What is claimed is:

1. A coupling device for connection to a member, comprising:

a coupling element defining a longitudinal axis and a passage extending therethrough generally along the longitudinal axis, said passage being bounded by a side wall having a first end and a second end, said side wall defining a first slot extending from said first end toward said second end and a second slot extending from said second end toward said first end, a portion of said second slot being positioned proximately adjacent and longitudinally overlapping a portion of said first slot; and a compression element at least partially formed of a shape-memory material and being disposed about said coupling element, said compression element having a first configuration and a second memorized configuration, said second configuration contracting about said coupling element and compressing said side wall against the member to thereby limit movement of the member relative to said coupling element.

2. The device of claim 1, wherein said first and second slots are aligned substantially parallel.

3. The device of claim 2, wherein said first and second slots are aligned generally along the longitudinal axis of said coupling element.

4. The device of claim 1, wherein said first slot includes a forked portion having first and second prongs, said portion of said second slot being positioned intermediate said first and second prongs.

5. The device of claim 4, wherein said second slot has a narrow end opening at said second end and a wide end positioned intermediate said first and second prongs so as to define a tear drop shape.

6. The device of claim 5, wherein said forked portion has a shape complementary to said shape of said second slot.

7. The device of claim 4, wherein said second slot terminates at a location adjacent a base of said forked portion, and wherein said first and second prongs terminate at a location adjacent said second end.

8. The device of claim 1, wherein said side wall defines a second pair of slots configured substantially similar and positioned generally opposite said first and second slots.

9. The device of claim 1, wherein the member has a first connecting portion, said coupling element being adapted for connection to a second member having a second connecting portion.

10. The device of claim 9, wherein said first connecting portion is received within said passage adjacent said first end, said second connecting portion being received within said passage adjacent said second end, said first and second connecting portions being aligned generally along the longitudinal axis of said coupling element.

11. The device of claim 10, wherein said first slot terminates at a location adjacent said second end, and wherein said second slot terminates at a location adjacent said first end.

12. The device of claim 9, wherein said first connecting portion is received within said passage adjacent said first end and aligned generally along the longitudinal axis of said coupling element, said second connecting portion being at least partially received within said passage adjacent said second end and aligned generally transverse to the longitudinal axis of said coupling element.

13. The device of claim 12, wherein said coupling element defines a channel extending laterally therethrough and sized to receive at least a portion of said second connecting portion therein, said channel being in communication with said passage and having an opening at said second end for receiving said at least a portion of said second connecting portion.

14. The device of claim 13, wherein said channel is defined by a portion of said second slot.

15. The device of claim 14, wherein said first slot terminates at a location adjacent said channel, and wherein said second slot terminates at a location adjacent said first end.

16. The device of claim 13, further comprising a locking element at least partially formed of a shape-memory material and being disposed about said coupling element adjacent said channel, said locking element having a first configuration and a second memorized configuration, said second configuration of said locking element contracting about said coupling element and compressing said side wall against said at least a portion of said second connecting portion to thereby limit movement of said second member relative to said coupling element.

17. The device of claim 16, wherein the shape-memory material of said compression element and the shape-memory material of said locking element have the same composition.

18. The device of claim 1, wherein said first and second configurations of said coupling device occur at different temperatures.

19. The device of claim 1, wherein said shape-memory material exhibits a stress-induced martensite behavior, said shape-memory material having a stress-induced martensitic state, said shape-memory material being in said stress-induced martensitic state when said coupling device is in said first configuration.

20. A spinal fixation system, comprising:
an elongate member for placement adjacent the spine;
a bone engaging member having an at least partially spherical-shaped head and a portion configured to engage a vertebral body;
a coupling element defining a longitudinal axis and a passage extending therethrough generally along the longitudinal axis, said passage being bounded by a side wall having a first end and a second end, said head of said bone engaging member being disposed within said passage, said coupling element defining a channel extending laterally therethrough and being sized to receive a portion of said elongate member therein, said channel being in communication with said passage and having an opening at said second end for receiving said portion of said elongate member, said side wall defining a first slot extending from said first end toward said second end and a second slot extending from said second end toward said first end, a portion of said second slot being positioned proximately adjacent and longitudinally overlapping a portion of said first slot; and
a compression element at least partially formed of a shape-memory material and being disposed about said coupling element, said compression element having a first configuration at one temperature and a second memorized configuration temperature, said second configuration contracting about said coupling element and compressing said side wall against said head to thereby limit movement of said bone engaging member relative to said coupling element.

21. The system of claim 20, wherein said first and second slots are aligned substantially parallel.

22. The system of claim 21, wherein said first and second slots are aligned generally along the longitudinal axis of said coupling element.

23. The device of claim 20, wherein said first slot includes a forked portion having first and second prongs, said portion of said second slot being positioned intermediate said first and second prongs.

24. The devise of claim 23, wherein said second slot terminates at a location adjacent a base of said forked portion, and wherein said first and second prongs terminate at a location adjacent said second end.

25. The device of claim 20, wherein said channel is defined by a portion of said second slot.

26. The device of claim 20, wherein said first slot terminates at a location adjacent said channel, and wherein said second slot terminates at a location adjacent said first end.

27. The system of claim 20, wherein said side wall defines a second pair of slots configured substantially similar t0 said first and second slots.

28. The system of claim 27, wherein said second pair of slots is positioned generally opposite said first and second slots.

29. The system of claim 20, wherein said side wall defines an inner annular recess along said passage for receiving said head therein so that the angular alignment of said bone engaging member may be variably adjusted relative to the longitudinal axis of said coupling element when said compression element is in said first configuration.

30. The system of claim 29, wherein said recess is positioned adjacent said first end, said channel positioned apart from said recess so that said head of said bone engaging member does not intersect said channel when said head is received within said recess.

31. The system of claim 29, wherein said side wall further defines an inner taper along said passage extending outwardly from said recess to said first end.

32. The system of claim 20, wherein said compression element is positioned adjacent said overlapping portions of said first and second slots.

33. The system of claim 20, further comprising a locking element at least partially formed of a shape-memory material and being disposed about said coupling element adjacent said channel, said locking element having a first configuration and a second memorized configuration, said second configuration of said locking element contracting about said coupling element and compressing said side wall against said portion of said elongate member to thereby limit movement of said elongate member relative to said coupling element.

34. The system of claim 33, wherein said coupling element includes a pair of opposing fingers extending from said second end generally along the longitudinal axis, each of said fingers having a rounded portion facing outwardly from said channel, said locking element being an oblong ring defining curved inner surfaces corresponding to said rounded portions and generally flat inner surfaces positioned intermediate said curved inner surfaces.

35. The system of claim 33, wherein the shape-memory material of said compression element and the shape-memory material of said locking element have the same composition.

36. The system of claim 20, wherein said head includes a truncated upper surface and defines a tool receiving recess extending from said upper surface.

37. A coupling device for connection to a member, comprising:
a coupling element defining a longitudinal axis and a passage extending therethrough generally along the longitudinal axis, said coupling element including slot means for rendering said passage collapsible, said slot means comprising a first slot and a second slot, said first slot including a forked portion having first and second prongs, at least a portion of said second slot being positioned intermediate said first and second prongs; and
shape-memory means cooperating with said coupling element for allowing movement of the member relative to said coupling element when in one configuration and limiting movement of the member relative to said coupling element when in another configuration.

38. The device of claim 37, wherein the member and said coupling element include means for allowing angular variation therebetween when said shape-memory means is in said one configuration.

39. The device of claim 37, wherein said forked portion has a shape corresponding to a shape of said at least a portion of said second slot.

40. A coupling device for connection to a member, comprising:
a coupling element defining a longitudinal axis and including a first longitudinal segments and a second longitudinal segment, said first and second longitudinal segment defining a passage extending through said coupling element generally along the longitudinal axis, said first and second longitudinal segments being connected by a pair of narrow sections of material; and
a compression element at least partially formed of a shape-memory material and being disposed about at least a portion of said segments, said compression element having a first configuration and a second memorized configuration, said second configuration contracting about said at least a portion of said segments and compressing said segments against the member to thereby limit movement of the member relative to said coupling element.

41. The device of claim 40, wherein each of said narrow sections of material has first and second edges extending generally along the longitudinal axis.

42. The device of claim 41, wherein said first and second edges are aligned substantially parallel and generally along the longitudinal axis of said coupling element.

43. The device of claim 40, wherein at least one of said narrow sections of material is substantially U-shaped.

44. The device of claim 43, wherein said at least one of said narrow sections of material has an inner edge and an outer edge, said inner and outer edges being aligned generally along the longitudinal axis of said coupling element.

45. The device of claim 40, wherein said pair of narrow sections of material are positioned generally opposite one another.

46. The device of claim 45, wherein said first and second longitudinal segments are longitudinal halves.

47. The device of claim 41, wherein said coupling element has a first end and an opposing second end, said first edge extending from said first end and terminating at a location adjacent said second end, said second edge extending from said second end and terminating at a location adjacent said first end.

48. A coupling device for connection to a member, comprising:
a coupling element defining a longitudinal axis and a passage extending therethrough generally along the longitudinal axis, said passage being bounded by a side wall having a first end and a second end, said side wall defining a first slot and a second slot, said first slot extending from said first end and including first and second segments extending toward said second end, said second slot extending from said second end toward said first end and being at least partially positioned intermediate said first and second segments of said first slot; and
a compression element at least partially formed of a shape-memory material and being disposed about said coupling element, said compression element having a first configuration and a second memorized configuration, said second configuration contracting about said coupling element and compressing said side wall against the member to thereby limit movement of the member relative to said coupling element.

49. The device of claim 48, wherein a portion of said second slot is positioned proximately adjacent and longitudinally overlapping a portion of each of said first and second segments of said first slot.

50. The device of claim 48, wherein said first and second segments of said first slot are aligned generally along the longitudinal axis of said coupling element.

51. The device of claim 48, wherein said first slot includes a first portion extending from said first end and a second portion in communication with said first portion and extending toward said second end, said second portion defining said first and second segments.

52. The device of claim 51, wherein said second portion of said first slot is substantially U-shaped.

53. The device of claim 51, wherein said second slot terminates at a location adjacent a base of said second portion of said first slot, and wherein said first and second segments of said first slot terminate at a location adjacent said second end.

54. The device of claim 48, wherein said second slot has a narrow end opening at said second end and a wide end positioned intermediate said first and second segments so as to define a tear drop shape.

55. The device of claim 48, wherein said side wall defines a second pair of slots configured substantially similar to and positioned generally opposite said first and second slots.

56. The device of claim 48, wherein said first and second configurations of said coupling element occur at different temperatures.

57. The device of claim 48, wherein said shape-memory material exhibits a stress-induced martensite behavior, said shape-memory material having a stress-induced martensitic state, said shape-memory material being in said stress-induced martensitic state when said coupling element is in said first configuration.

* * * * *